(12) United States Patent
Gillespie et al.

(10) Patent No.: US 11,408,840 B2
(45) Date of Patent: Aug. 9, 2022

(54) HIGH THROUGHPUT INTERROGATION OF PHYSIOCHEMICAL PROPERTIES OF A PROTEIN

(71) Applicant: Just Biotherapeutics, Inc., Seattle, WA (US)

(72) Inventors: Alison J. Gillespie, Seattle, WA (US); Jeremy M. Shaver, Lake Forest Park, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 722 days.

(21) Appl. No.: 16/445,090

(22) Filed: Jun. 18, 2019

(65) Prior Publication Data

US 2020/0003714 A1 Jan. 2, 2020

Related U.S. Application Data

(60) Provisional application No. 62/691,578, filed on Jun. 28, 2018.

(51) Int. Cl.
| | | |
|---|---|---|
| *G01N 25/04* | (2006.01) | |
| *C07K 16/06* | (2006.01) | |
| *G16B 45/00* | (2019.01) | |
| *G16B 15/20* | (2019.01) | |

(52) U.S. Cl.
CPC ........... *G01N 25/04* (2013.01); *C07K 16/065* (2013.01); *G16B 15/20* (2019.02); *G16B 45/00* (2019.02); *C07K 2317/14* (2013.01); *C07K 2317/41* (2013.01)

(58) Field of Classification Search
CPC ................................ G01N 25/04; G16B 15/20
See application file for complete search history.

(56) References Cited

U.S. PATENT DOCUMENTS

| | | |
|---|---|---|
| 9,133,343 B2 | 9/2015 | Patton et al. |
| 9,366,677 B2 | 6/2016 | Stark et al. |
| 2014/0206092 A1 | 7/2014 | Stark et al. |
| 2014/0315190 A1 | 10/2014 | Rhodes et al. |
| 2015/0125444 A1 | 5/2015 | Tsui et al. |
| 2015/0212182 A1 | 7/2015 | Nielsen et al. |
| 2017/0204199 A1 | 7/2017 | Sanches et al. |

FOREIGN PATENT DOCUMENTS

| | | | | |
|---|---|---|---|---|
| CN | 105324396 A | * | 2/2016 | ......... A61K 39/3955 |
| CN | 106353295 A | * | 1/2017 | ......... G01N 21/6486 |
| EP | 2753927 B1 | | 7/2014 | |
| WO | 0226891 A1 | | 4/2002 | |
| WO | 2011065980 A2 | | 6/2011 | |
| WO | 2013034160 A1 | | 3/2013 | |
| WO | 2014144360 A2 | | 9/2014 | |
| WO | 2014144360 A3 | | 9/2014 | |
| WO | WO-2018050027 A1 | * | 3/2018 | ........... A61K 39/395 |

OTHER PUBLICATIONS

Alsenaidy, Mohammad A. et al, "Physical stability comparisons of IgG1-Fc variants: effects of N-glycosylation site occupancy and Asp/Gln residues at site Asn 297," J. Pharm. Sci. Jun. 2014: 103(6); p. 1613-1627, published online Apr. 16, 2014.

\* cited by examiner

*Primary Examiner* — David Z Huang

(74) *Attorney, Agent, or Firm* — Law Offices of Nisan Steinberg

(57) ABSTRACT

Disclosed are methods for interrogating the physiochemical properties of a protein of interest, including method for predicting the stability of a protein at low pH, such as may be encountered during a manufacturing viral inactivation step.

18 Claims, 7 Drawing Sheets

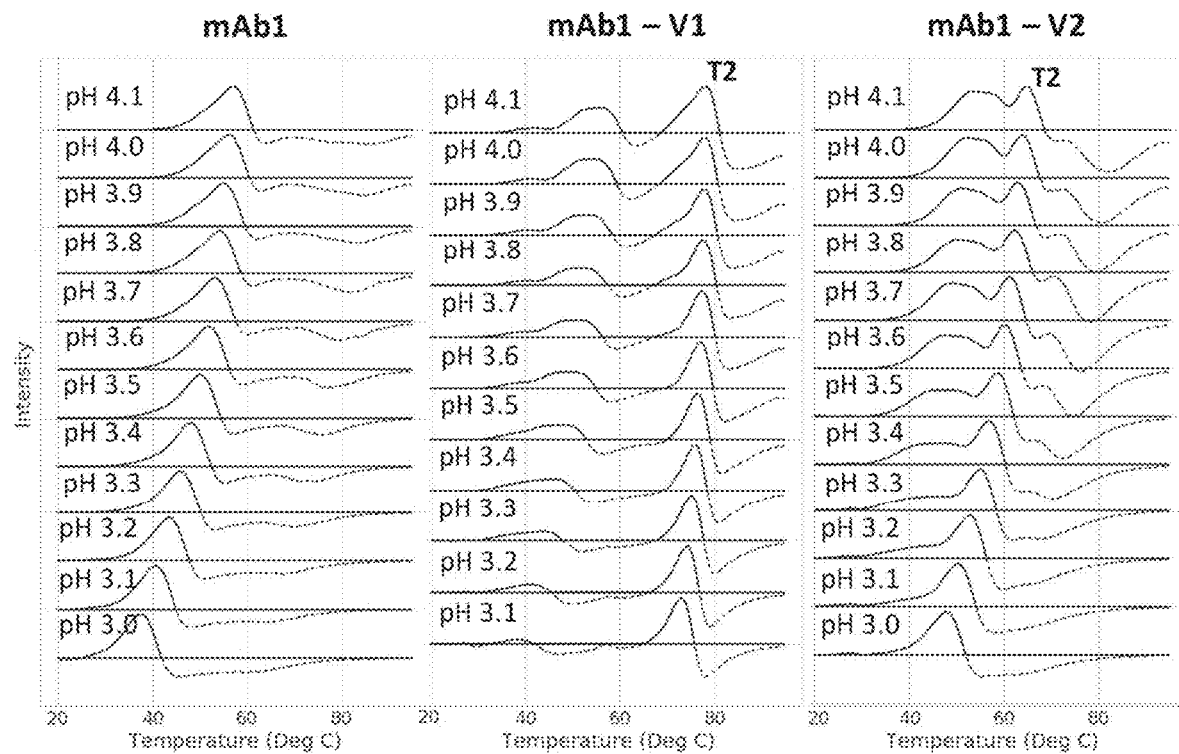

HIGH THROUGHPUT INTERROGATION OF PHYSIOCHEMICAL PROPERTIES OF A PROTEIN

CROSS-REFERENCES TO RELATED APPLICATIONS

This non-provisional patent application claims priority from U.S. Provisional Application Ser. No. 62/691,578, filed Jun. 28, 2018, which is incorporated by reference in its entirety.

BACKGROUND OF THE INVENTION

1. Field of the Invention

This invention relates to the field of high throughput screening methods to determine the physiochemical properties of proteins, particularly therapeutic proteins, and their manufacturability.

2. Discussion of the Related Art

Antibodies and other target binding proteins (collectively known as "biologics") are biologically and commercially significant polypeptides that bind with great specificity and affinity to a particular target molecule or antigen. The clinical value of certain antibodies as therapeutic molecules has long been recognized. However, antibodies and other biologics that otherwise can be useful therapeutic molecules can also exhibit many undesirable properties disallowing for easy manufacture, storage and therapeutic delivery. (See, e.g., Daugherty, A. L. et al., *Formulation and delivery issues for monoclonal antibody therapeutics*, Advanced Drug Delivery Reviews 58(5-6):686-706 (2006); Vazquez-Rey, M., & Lang, D. a. (2011). Aggregates in monoclonal antibody manufacturing processes. Biotechnology and Bioengineering, 108(7), 1494-1508 (2011)).

For example, some protein molecules or variants turn out to be unstable under certain physiochemical conditions that are encountered during common manufacturing steps, such as low pH viral inactivation, which can seriously affect ultimate production yield.

A typical bench scale experiment by traditional techniques, such as differential scanning calorimetry (DSC), to interrogate or predict the physiochemical properties of a protein of interest for development as a potential therapeutic commonly requires gram quantities of the protein.

Differential scanning fluorimetry (DSF) is a high throughput, low cost technique used to study protein-ligand interactions and assess protein unfolding temperatures as a protein is subjected to an increasing thermal gradient. (See, e.g., Bornarth et al., *Methods for Dye Selection for Protein Melt Temperature Determinations*, US2014/0315190 A1; Stark et al., *Methods for Analyzing Biological Macromolecular Complexes and Use Thereof*, U.S. Pat. No. 9,366,677B2; EP2753927B1; Sanches et al., *Modified Antigen Binding Polypeptide Constructs and Uses Thereof*, US2017/204199 A1).

The DSF technique has also been employed to study protein aggregate formation. (See, e.g., Patton et al., *Novel Dyes And Compositions, And Processes For Using Same In Analysis Of Protein Aggregation And Other Applications*, U.S. Pat. No. 9,133,343).

DSF uses an extrinsic hydrophobic dye to monitor protein thermal unfolding. The DSF technique uses microgram quantities of material as compared to the DSC technique. Studies have shown good correlation between the two techniques. (See, e.g., He, F et al., *High Throughput thermostability screening of monoclonal antibody formulations*, J. Pharm. Sci. 99 (4): 1707-1720 (2010)).

There is a need for high throughput methods of interrogating the physiochemical properties of proteins of interest in early development molecule assessments when protein mass quantities are limited. This and other benefits the present invention provides.

SUMMARY OF THE INVENTION

The present invention relates to methods of interrogating the physiochemical properties of a protein of interest. Herein we demonstrate the use of differential scanning fluorimetry (DSF) to assess or predict a protein's stability under physiochemical stress to quickly screen candidates during early protein molecule design activities that will fit into industry standard manufacturing platforms, for example, under the low pH conditions characteristic of viral inactivation platforms. While typical bench scale studies require milligram to gram quantities of protein product, the present invention allows high throughput assessment with only 50-100 μg of product.

In one aspect, the invention is directed to a method for predicting the stability of a protein of interest at low pH, The inventive method involves the steps of
(a) heating to a continuous set of temperatures in the range of about 20° C. to about 95° C. a first reaction mixture comprising a hydrophobic fluorescent dye and the protein of interest, at a first pH value in the range of about pH 4.0 to about pH 4.2, and:
  (i) detecting fluorescence of the dye over the range of temperatures to obtain a first fluorescence curve;
  (ii) obtaining the first derivative of the first fluorescence curve; and
  (iii) determining the temperature transitions of the protein of interest, at the first pH value, from the first derivative of the first fluorescence curve;
(b) heating to a continuous set of temperatures in the range of about 20° C. to about 95° C. one or more second reaction mixture(s) comprising the hydrophobic fluorescent dye and the protein of interest, at one or more different second pH value(s) between about pH 2.9 to about pH 4.0, each different second pH value being lower than the first pH value, and:
  (i) detecting fluorescence of the dye in each of the one or more second reaction mixture(s) over the range of temperatures to obtain a second fluorescence curve for each second reaction mixture;
  (ii) obtaining the first derivative of each second fluorescence curve; and
  (iii) determining the temperature transitions of the protein of interest, at the one or more different second pH value(s), from the first derivative(s) of the second fluorescence curve(s); and
(c) comparing the temperature transition peaks of the protein of interest at the first pH value and at the one or more different second pH value(s), wherein, if a temperature transition peak present at the first pH value is absent or shifted at one or more of the different second pH value(s), the protein of interest is predicted to display poor stability at low pH. Thus, in this aspect, the present invention is useful in predicting whether a protein of interest is a suitable candidate for low pH viral inactivation during manufacturing.

In another aspect, the present invention relates to a method for interrogating the physiochemical properties of a protein of interest, which avoids ambiguous peak-fitting approaches to quantification of DSF thermograms. The present invention employs two simple-to-calculate metrics which describe the shape of the thermogram and produce values that are related to the thermal stability of the protein molecule under study. The values, which we have named the Weighted Shoulder Score (WSS) and Weighted Leader Score (WLS) provide convenient and accurate metrics to compare molecules. In this aspect, the method involves the steps of:

(a) heating to a continuous set of temperatures, each temperature being a value of T in the range of about 20° C. to about 95° C., a reaction mixture comprising a hydrophobic fluorescent dye and the protein of interest in a buffer, which contains a physiochemical stressor of interest at a reference concentration greater than or equal to zero, and:
(i) detecting fluorescence of the dye over the range of temperatures to obtain a first fluorescence curve; and
(ii) obtaining the first derivative of the first fluorescence curve;
(b) heating to a continuous set of temperatures in the range of about 20° C. to about 95° C. one or more second reaction mixture(s) comprising the hydrophobic fluorescent dye and the protein of interest, at one or more different second concentration value(s) of the physiochemical stressor of interest, each different second concentration value being greater than the reference concentration, and:
(i) detecting fluorescence of the dye in each of the one or more second reaction mixture(s) over the range of temperatures to obtain a second fluorescence curve for each second reaction mixture; and
(ii) obtaining the first derivative of each second fluorescence curve;
(c) determining the temperature transitions of the protein of interest from the first derivative of the first fluorescence curve or from the first derivative of each second fluorescence curve, or both, which comprises:
(i) locating on the first derivative of the first fluorescence curve a lowest temperature peak (the $T_1$ peak of the first fluorescence curve) having a maximum intensity of at least about 30% of the maximum intensity peak of the first derivative of the fluorescence curve, wherein the fluorescence intensity of the $T_1$ peak of the first fluorescence curve is In, and the temperature at which the maximum $I_{T1}$ occurs is $T_{T1}$ of the first fluorescence curve; and
(ii) for each of the one or more second fluorescence curve(s), finding a peak closest in temperature to the:
(1) $T_{T1}$ of the first fluorescence curve; or
(2) $T_{T1}$ of a different second fluorescence curve obtained from a different second reaction mixture with a different second concentration value closest to its second concentration value;
and designating that peak the $T_1$ peak of the second fluorescence curve, wherein the fluorescence intensity of the $T_1$ peak of each second fluorescence curve is the $I_{T1}$ of the second fluorescence curve and the temperature at which the maximum $I_{T1}$ of the second fluorescence curve occurs is the $T_{T1}$ of the second fluorescence curve, and:
(iii) calculating the fluorescence intensity value (I) of all points of the first derivative of each of the first fluorescence curve and the one or more second fluorescence curve(s) normalized to its $I_{T1}$ ($I_{norm}$), wherein $I_{norm} = I/I_{T1}$;
(iv) calculating a relative temperature value ($T_{rel}$) of all points of the first derivative of each fluorescence curve relative to its $T_{T1}$, wherein, $T_{rel} = T - T_{T1}$;
(v) calculating a weight ($W_{WSS}$) of all points of the first derivative of the fluorescence curve, wherein:

$$W_{WSS} = \begin{cases} T_{rel}^2, & \text{if } (T_{rel} > 0 \text{ and } I_{norm} > 0) \\ 0, & \text{otherwise} \end{cases};$$

(vi) subsequently calculating a scalar weighted shoulder score (WSS), wherein:

$$WSS = \sqrt{I_{norm} W_{WSS}},$$

wherein the position and shape of a second temperature transition ($T_2$) peak and/or a third temperature transition ($T_3$) peak characteristic of the unfolding of the protein of interest are detected as increases in the scalar WSS value; and
(d) comparing the temperature transition peaks of the protein of interest at the reference concentration and at the one or more different second concentration value(s) of the physiochemical stressor of interest, wherein, if a temperature transition peak present at the reference concentration is absent or shifted at one or more of the different second concentration value(s) of the physiochemical stressor of interest, the protein of interest is shown to display poor stability in response to the physiochemical stressor of interest.

In the foregoing aspect, involving calculation of weighted shoulder score values (WSS) values, the present invention allows detection of transitions that would typically go undetected by previously available methods, such as peak fitting. WSS and WLS values are also useful continuous-response metrics for developing machine-learning models that predict the thermal stability of protein molecules and their variants.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 7A-C shows stacked plots of the DSF low pH screen results for mAb1 and two mAb1 sequence variants (mAb1-V1 and mAb1-V2). The two sequence variants had significant shifts in the DSF profiles with resolved T2 peaks, compared to the mAb1 parent that had a single transition. Additionally, the two sequence variants had substantial differences in the transition 2 temperature, implying that the mAb1-V1 sequence differences stabilized the CH3 and/or Fab domains of the molecule when compared to mAb1-V2.

DETAILED DESCRIPTION OF EMBODIMENTS

Figure 1:
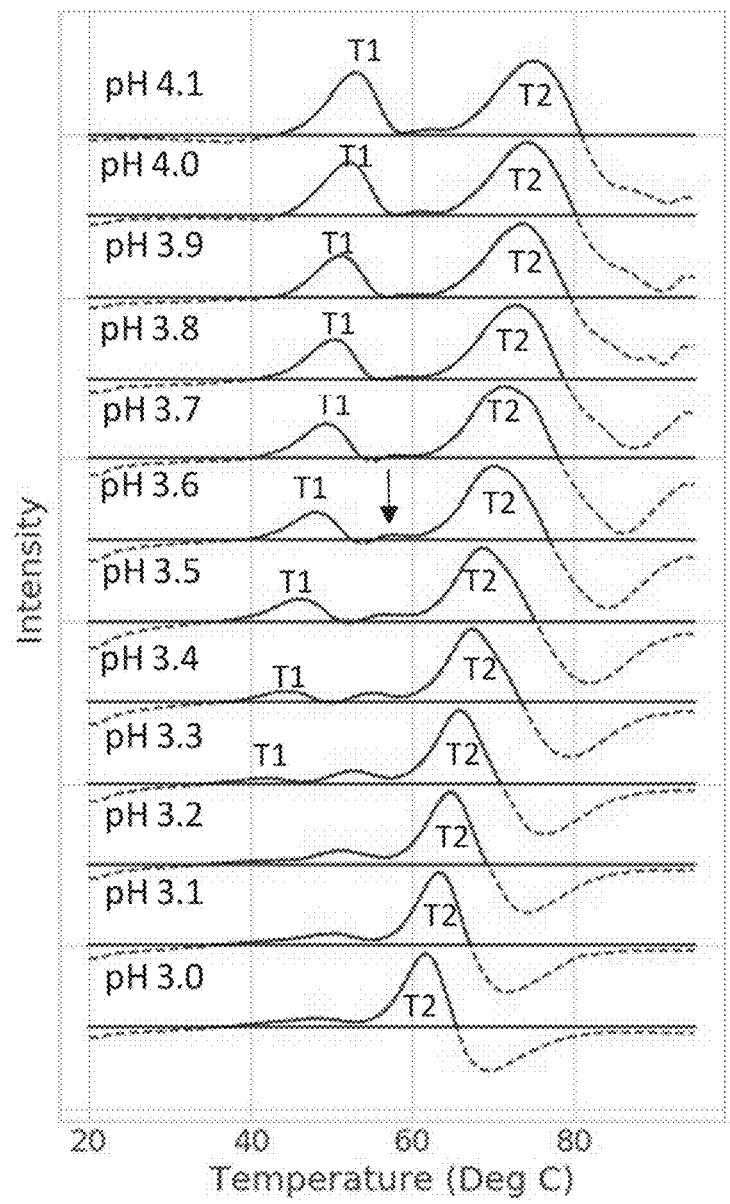
FIG. 1 shows representative stacked plots of the DSF pH screen results for Protein 5 (an IgG) at various pH values. The DSF pH screen demonstrated that the transition 1 (T1—associated with CH2 domain) and transition 2 (T2—associated with CH3 and Fab domains) decrease in temperature as a function of pH. At pH 3.2, the T1 signal was no longer evident indicating a change in structure resulting in dissociation from the protein of the hydrophobic dye (Sypro® Orange) in the reaction mixture. At pH 3.6 an intermediate transition was detected at approximately 58° C. (black arrow). For proteins with pH stable Fab domains, the more pH sensitive CH3 domain begins to unfold at a lower temperature, with decreasing pH conditions. This shift in CH3 unfolding temperature allowed this domain to be resolved from the Fab domain transition peak (T2 peak).

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a reaction mixture" includes a plurality of reaction mixtures.

In one aspect the invention includes a method for predicting the stability of a protein at low pH; the method comprises heating to a continuous set of temperatures in the range of about 20° C. to about 95° C. a first reaction mixture comprising a hydrophobic fluorescent dye and a protein of interest, at a first pH value in the range of about pH 4.0 to about pH 4.2. The term "low pH" means a pH value of about pH 3.7 or lower. (See, e.g., Chinniah, S et al., *Characterization of operating parameters for XMuLV inactivation by low pH treatment*, Biotechnol Prog. 32(1):89-97 (2016).

A protein of interest, such as an antibody or fusion protein, for purposes of the present invention, whether it includes a variant or parental antibody amino acid sequence, is typically produced by recombinant expression technology, although it can also be a naturally occurring protein.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, proteins can be derivatized as described herein and by other well-known organic chemistry techniques.

A "variant" of a polypeptide (e.g., an immunoglobulin, or an antibody, or a fusion protein) comprises an amino acid sequence wherein one or more amino acid residues are inserted into, deleted from and/or substituted into the amino acid sequence relative to another polypeptide sequence. Variants can include variants of fusion proteins.

The term "fusion protein" indicates that the protein includes polypeptide components derived from more than one parental protein or polypeptide. Typically, a fusion protein is expressed from a "fusion gene" in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein. Fusion proteins incorporating an antibody or an antigen-binding portion thereof are known.

A "secreted" protein refers to those proteins capable of being directed to the endoplasmic reticulum (ER), secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments, the antibody protein of interest can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes, or, in vitro, is dissolved, or is capable of being dissolved in an aqueous buffer under physiological conditions without forming significant amounts of insoluble aggregates (i.e., forms aggregates less than 10%, and typically less than about 5%, of total protein) when it is suspended without other proteins in an aqueous buffer of interest under physiological conditions, such buffer not containing an ionic detergent or chaotropic agent, such as sodium dodecyl sulfate (SDS), urea, guanidinium hydrochloride, or lithium perchlorate. In contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc., or in an in vitro aqueous buffer under physiological conditions forms significant amounts of insoluble aggregates (i.e., forms aggregates equal to or more than about 10% of total protein) when it is suspended without other proteins (at physiologically compatible temperature) in an aqueous buffer of interest under physiological conditions, such buffer not containing an ionic detergent or chaotropic agent, such as sodium dodecyl sulfate (SDS), urea, guanidinium hydrochloride, or lithium perchlorate.

In another aspect, the invention is directed to a method for interrogating the physiochemical properties of a protein of interest, particularly with respect to a physiochemical stressor of interest. The method is useful, for example, for high throughput interrogation of proteins of interest to facilitate the selection of protein variants with relatively high physical and/or chemical stability for formulation as a drug product.

A "stable" formulation of a protein is one in which the protein therein, e.g., an antibody or fusion protein, essentially retains its physical stability and/or chemical stability and/or biological activity upon processing (e.g., ultrafiltration, diafiltration, other filtering steps, vial filling), transportation, and/or storage of the antibody drug substance and/or drug product. Together, the physical, chemical and biological stability of the protein in a formulation embody the "stability" of the protein formulation, which is specific to the conditions under which the formulated drug product (DP) is stored. For instance, a drug product stored at subzero temperatures would be expected to have no significant change in either chemical, physical or biological activity while a drug product stored at 40° C. would be expected to have changes in its physical, chemical and biological activity with the degree of change dependent on the time of storage for the drug substance or drug product. The configuration of the protein formulation can also influence the rate of change. For instance, aggregate formation is highly influenced by protein concentration with higher rates of aggregation observed with higher protein concentration. Excipients are also known to affect stability of the drug product with, for example, addition of salt increasing the rate of aggregation for some proteins while other excipients such as sucrose are known to decrease the rate of aggregation during storage. Instability is also greatly influenced by pH giving rise to both higher and lower rates of degradation depending on the type of modification and pH dependence.

Various analytical techniques for measuring protein stability are available in the art and are reviewed, e.g., in Wang, W. (1999), *Instability, stabilization and formulation of liquid protein pharmaceuticals*, Int J Pharm 185:129-188. Stability can be measured at a selected temperature for a selected time period. For rapid screening, for example, the formulation may be kept at 40° C. for 2 weeks to 1 month, at which time stability is measured. Where the formulation is to be stored at 2-8° C., generally the formulation should be stable at 30° C. for at least 1 month, or 40° C. for at least a week, and/or stable at 2-8° C. for at least two years.

A protein "retains its physical stability" in a formulation if it shows minimal signs of changes to the secondary and/or tertiary structure (i.e., intrinsic structure), or aggregation, and/or precipitation and/or denaturation upon visual examination of color and/or clarity, or as measured by UV light scattering or by size exclusion chromatography, or other suitable methods. Physical instability of a protein, i.e., loss of physical stability, can be caused by oligomerization resulting in dimer and higher order aggregates, subvisible, and visible particle formation, and precipitation. The degree of physical degradation can be ascertained using varying techniques depending on the type of degradant of interest. Dimers and higher order soluble aggregates can be quantified using size exclusion chromatography, while subvisible particles may be quantified using light scattering, light obscuration or other suitable techniques.

A protein "retains its chemical stability" in a formulation, if the chemical stability at a given time is such that covalent bonds are not made or broken, resulting in changes to the primary structure of the protein component, e.g., antibody. Changes to the primary structure may result in modifications of the secondary and/or tertiary and/or quaternary structure of the protein and may result in formation of aggregates or reversal of aggregates already formed. Typical chemical modifications can include isomerization, deamidation, N-terminal cyclization, backbone hydrolysis, methionine oxidation, tryptophan oxidation, histidine oxidation, beta-elimination, disulfide formation, disulfide scrambling, disulfide cleavage, and other changes resulting in changes to the primary structure including D-amino acid formation. Chemical instability, i.e., loss of chemical stability, may be interrogated by a variety of techniques including ion-exchange chromatography, capillary isoelectric focusing, analysis of peptide digests and multiple types of mass spectrometric techniques. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by charge-based methods, such as, but not limited to, ion-exchange chromatography, capillary isoelectric focusing, or peptide mapping.

Loss of physical and/or chemical stability may result in changes to biological activity as either an increase or decrease of a biological activity of interest, depending on the modification and the protein being modified. A protein "retains its biological activity" in a formulation, if the biological activity of the protein at a given time is within about 30% of the biological activity exhibited at the time the formulation was prepared. Activity is considered decreased if the activity is less than 70% of its starting value. Biological assays may include both in vivo and in vitro based assays such as ligand binding, potency, cell proliferation or other surrogate measure of its biopharmaceutical activity.

The term "naturally occurring," where it occurs in the specification in connection with biological materials such as polypeptides, nucleic acids, host cells, and the like, refers to materials which are found in nature.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., *Molecular Cloning. A Laboratory Manual*. Cold Spring Harbor Laboratory, Cold Spring Harbor, N.Y. (1982). A "recombinant DNA molecule," is comprised of segments of DNA joined together by means of such molecular biological techniques.

The term "recombinant protein" or "recombinant polypeptide" as used herein refers to a protein molecule, e.g., an antibody or fusion protein, which is expressed using a recombinant DNA molecule. A "recombinant host cell" is a cell that contains and/or expresses a recombinant nucleic acid.

The term "heating to a continuous set of temperatures" means that a reaction mixture is heated through a range of temperatures from a lowest temperature to a highest temperature, whether in a continuous gradient of temperatures, or in a progressive step-wise fashion, but still from a lowest temperature to highest temperature.

A "reaction mixture" is an aqueous mixture containing all the reagents and factors necessary, which under the conditions of incubation, permit an in vitro biochemical reaction of interest to occur, such as a covalent or non-covalent binding, or a dissociation. For example, the in vitro biochemical reaction can include non-covalent binding of a fluorescent dye to a protein of interest or the dissociation of such a dye from the protein. Within the scope of the invention, the reaction mixture can include a "physiochemical stressor," which is a modified physical and/or chemical condition or additive for the purpose of interrogating the structure and/or behavior of the protein of interest. For example, physiochemical stressors include, but are not limited to, pH, temperature, pressure, shear force, cavitation, buffer salinity or conductivity, chemical denaturants (e.g., guanidine-HCl or urea), detergents, surfactants, heavy metals, metalloids, oxidants, reductants or reducing environments, free radicals and/or light exposure. The reaction mixture can be contained in a cuvette or in a chamber or well of a 96-well or 384-well plate to facilitate presentation to a high throughput fluorescence detector, which may be automated.

A "hydrophobic fluorescent dye" is a dye that changes its response to excitation within a hydrophobic environment compared to an aqueous environmant, e.g., enhanced or diminished fluorescence intensity, shifting of excitation and/or emission wavelength, and/or modification of its characteristic emission lifetime. Useful examples include, but are not limited to, Sypro® Orange Dye (ThermoFisher Scientific); 4-(dicyanovinyl)julolidine (DCVJ); a thiol-reactive probe, such as boron-dipyrromethene (BODIPY) FL 1-cystine (BFC); N-[4-(7-diethylamino-4-methyl-3-coumarinyl) phenyl] maleimide (CPM); or other fluorescent dyes known in the art. (See, e.g., Menzen, T, Friess W, 2013 "High-throughput melting-temperature analysis of a monoclonal antibody by differential scanning fluorimetry in the presence of surfactants" J Phar Sci. 102(2):415-428 (2013); Hofmann, L et al., *An effective thiol-reactive probe for differential scanning fluorimetry with a standard RT-PCR device*, Anal. Biochem. 499:63-65 (2016); Alexandrov, A I et al., *Microscale fluorescent thermal stability assay for membrane proteins*, Structure. 16(3):351-359 (2008); Patton et al., *Dyes and compositions, and processes for using same in analysis of protein aggregation and other applications*, U.S. Pat. No. 9,133,343). Any commercially available fluorescence detector can be used to detect and measure fluorescence from the dye in the reaction mixture, preferably a detector suitable for high throughput fluorescence detection. The raw fluorescence data from the detector is assembled and recorded, preferably by a digital data processor (but manual processing of data is also encompassed within the invention), and fluorescence curves of the fluorescence data from each reaction mixture with respect to the temperature are obtained or constructed. Then, obtaining the first derivative (i.e., numerical first derivative) of the first fluorescence curve and/or obtaining the first derivative (i.e., numerical first derivative) of each second fluorescence curve is accomplished by applying the Savitzky-Golay algorithm or a similar algorithm. (See, e.g., Savitzky, A. and Golay, M. J. E., *Smoothing and Differentiation of Data by Simplified Least Squares Procedures*, Analytical Chemistry 36 (8): 1627-39 (1964); Savitzky, A., *A Historic Collaboration, Analytical Chemistry* 61 (15): 921 A-3 A (1989); Steinier. J. et al., *Smoothing and differentiation of data by simplified least square procedure*, Analytical Chemistry. 44 (11): 1906-9 (1972)).

The inventive methods involve determining the temperature transitions of the protein of interest from the first derivative of the first fluorescence curve and/or from the first derivative of each second fluorescence curve. A "temperature transition," or "temperature transitions," are temperature(s) at which the protein molecule unfolds and exposes hydrophobic regions isolated from solvent exposure by the native-state tertiary protein structure.

The inventive method involves locating, or finding, on the first derivative of the first fluorescence curve, and/or on the first derivative of each of the one or more second fluorescence curve(s), a "temperature peak" (or interchangeably herein, a "temperature transition peak" or, simply, a "peak"), which is at least a local maximum value of a dependent variable with lesser values on each side, such as a peak in the fluorescence signal value and/or its rate of change, as the case may be, at a corresponding temperature (i.e., the independent variable).

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

A "promoter" is a region of DNA including a site at which RNA polymerase binds to initiate transcription of messenger RNA by one or more downstream structural genes. Promoters are located near the transcription start sites of genes, on the same strand and upstream on the DNA (towards the 5' region of the sense strand). Promoters are typically about 100-1000 bp in length.

An "enhancer" is a short (50-1500 bp) region of DNA that can be bound with one or more activator proteins (transcription factors) to activate transcription of a gene.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the immunoglobulin (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

An expression cassette is a typical feature of recombinant expression technology. The expression cassette includes a gene encoding a protein of interest, e.g., a gene encoding an antibody sequence, such as an immunoglobulin light chain and/or heavy chain sequence. A eukaryotic "expression cassette" refers to the part of an expression vector that enables production of protein in a eukaryotic cell, such as a mammalian cell. It includes a promoter, operable in a eukaryotic cell, for mRNA transcription, one or more gene(s) encoding protein(s) of interest and a mRNA termination and processing signal. An expression cassette can usefully include among the coding sequences, a gene useful as a selective marker. In the expression cassette promoter is operably linked 5' to an open reading frame encoding an exogenous protein of interest; and a polyadenylation site is operably linked 3' to the open reading frame. Other suitable control sequences can also be included as long as the expression cassette remains operable. The open reading frame can optionally include a coding sequence for more than one protein of interest.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

Recombinant expression technology typically involves the use of a recombinant expression vector comprising an expression cassette and a mammalian host cell comprising the recombinant expression vector with the expression cassette or at least the expression cassette, which may for example, be integrated into the host cell genome.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (See, e.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., *Protein expression vector and utilization thereof*, U.S. Pat. No. 7,029,909; Ruben et al., 27 human secreted proteins, US 2003/0104400 A1). For expression of multi-subunit proteins of interest, separate expression vectors in suitable numbers and proportions, each containing a coding sequence for each of the different subunit monomers, can be used to transform a host cell. In other embodiments, a single expression vector can be used to express the different subunits of the protein of interest.

The term "host cell" means a cell that has been transformed, or is capable of being transformed, with a nucleic acid and thereby expresses a gene or coding sequence of interest. The term includes the progeny of the parent cell, whether or not the progeny is identical in morphology or in genetic make-up to the original parent cell, so long as the gene of interest is present. Any of a large number of available and well-known host cells may be used in the practice of this invention to obtain antibody variants, although mammalian host cells capable of post-translationally glycosylating antibodies are preferred. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Modifications can be made at the DNA level, as well. The peptide-encoding DNA sequence may be changed to codons more compatible with the chosen host cell. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

Within these general guidelines, microbial host cells in culture, such as bacteria (such as *Escherichia coli* sp.), and yeast cell lines (e.g., *Saccharomyces, Pichia, Schizosaccharomyces, Kluyveromyces*) and other fungal cells, algal or algal-like cells, insect cells, plant cells, that have been modified to incorporate humanized glycosylation pathways, can also be used to produce fully functional glycosylated antibody. However, mammalian (including human) host cells, e.g., CHO cells and HEK-293 cells, are particularly useful.

Examples of useful mammalian host cell lines are Chinese hamster ovary cells, including CHO-K1 cells (e.g., ATCC CCL61), CHO-S, DXB-11, DG-44, and Chinese hamster ovary cells/-DHFR (CHO, Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture (Graham et al, J. Gen Virol. 36: 59 (1977)); baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3 A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells, e.g., NS0 or sp2/0 mouse myeloma cells.

"Cell," "cell line," and "cell culture" are often used interchangeably and all such designations herein include cellular progeny. For example, a cell "derived" from a CHO cell is a cellular progeny of a Chinese Hamster Ovary cell, which may be removed from the original primary cell parent by any number of generations, and which can also include a transformant progeny cell. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Host cells are transformed or transfected with the above-described nucleic acids or vectors for production of polypeptides (including antigen binding proteins, such as antibodies) and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides, such as antibodies.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier, Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The host cells can be usefully grown in batch culture, fed-batch culture, intensified fed-batch culture (product retention perfusion), or in continuous culture systems employing liquid aqueous medium. Mammalian cells, such as CHO and BHK cells, are generally cultured as suspension cultures. That is to say, the cells are suspended in a liquid cell culture medium, rather than adhering to a solid support. In other embodiments, the mammalian host cells can be cultured on solid or semi-solid aqueous culture medium, for example, containing agar or agarose, to form a medium, carrier (or microcarrier) or substrate surface to which the cells adhere and form an adhesion layer. Another useful mode of production is a hollow fiber bioreactor with an adherent cell line. Porous microcarriers can be suitable and are available commercially, sold under brands, such as Cytoline®, Cytopore® or Cytodex® (GE Healthcare Biosciences).

"Cell culture medium" or "culture medium," used interchangeably, is a sterile medium suitable for growth of cells, and preferably animal cells, more preferably mammalian cells (e.g., CHO cells), in in vitro cell culture.

"Under physiological conditions" with respect to incubating buffers and immunoglobulins, or other binding assay reagents means incubation under conditions of temperature, pH, and ionic strength, that permit a biochemical reaction, such as a non-covalent binding reaction, to occur. Typically, the temperature is at room or ambient temperature up to about 37° C. and at pH 6.5-7.5.

A "domain" or "region" (used interchangeably herein) of a polynucleotide is any portion of the entire polynucleotide, up to and including the complete polynucleotide, but typically comprising less than the complete polynucleotide. A domain can, but need not, fold independently (e.g., DNA hairpin folding) of the rest of the polynucleotide chain and/or be correlated with a particular biological, biochemical, or structural function or location, such as a coding region or a regulatory region.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

Quantification of immunoglobulin protein (e.g., an antibody), is often useful or necessary in tracking protein. An antibody that specifically binds a domain of the antibody or antibodies of interest, particularly a specific monoclonal antibody, can therefore be useful for these purposes.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', $F(ab')_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

An "isolated" protein, e.g., an antibody or fusion protein, is one that has been identified and separated from one or more components of its natural environment or of a culture medium in which it has been secreted by a producing cell. In some embodiments, the isolated protein is substantially free from proteins or polypeptides or other contaminants that are found in its natural or culture medium environment that would interfere with its therapeutic, diagnostic, prophylactic, research or other use. "Contaminant" components of its natural environment or medium are materials that would interfere with diagnostic or therapeutic uses for the protein, e.g., an antibody, and may include enzymes, hormones, and other proteinaceous or nonproteinaceous (e.g., polynucleotides, lipids, carbohydrates) solutes. Typically, an "isolated protein" constitutes at least about 5%, at least about 10%, at least about 25%, or at least about 50% of a given sample. In some embodiments, the protein of interest, e.g., an antibody, will be purified (1) to greater than 95% by weight of protein, and most preferably more than 99% by weight, or (2) to homogeneity by SDS-PAGE, or other suitable technique, under reducing or nonreducing conditions, optionally using a stain, e.g., Coomassie blue or silver stain. Isolated naturally occurring antibody includes the antibody in situ within recombinant cells since at least one component of the protein's natural environment will not be present. Typically, however, the isolated protein of interest (e.g., an antibody) will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies that are antigen binding proteins are highly specific binders, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"). An "immunoglobulin" is a protein, but is not necessarily an antigen binding protein.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is an antigen binding protein. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (.kappa.) and lambda (.lamda.) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). An "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, V., and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the carboxy-terminus of the polypeptide. Heavy chains are classified as mu (µ), delta (δ), gamma (γ), alpha (α), and epsilon (ε), and define the antibody's isotype as IgM, IgD, IgG, IgA, and IgE, respectively. Heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (Fc.gamma.Rs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_{H1}$ and $C_{H2}$ domains of the antibody. The two heavy chain fragments are held together by two or more disulfide bonds and by hydrophobic interactions of the $C_{H3}$ domains.

The term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, th Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or "FR" residues are those variable region residues other than the hypervariable region residues.

The protein of interest can also be or include one or more antibody fragments. "Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10):1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')$_2$ fragment that has two "Single-chain Fv" or "scFv" antibody fragments comprising the $V_H$ and $V_L$ domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 1 13, Rosenburg and Moore eds., Springer-Verlag, New York, pp. 269-315 (1994).

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference in their entireties.

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Nati. Acad. Sci. USA 85:5879-5883, 1988). An "Fd" fragment consists of the $V_H$ and $C_{H1}$ domains.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "antigen binding protein" (ABP) includes antibodies or antibody fragments, as defined herein, that specifically bind a target ligand or antigen of interest.

In general, an antigen binding protein, e.g., an immunoglobulin protein, or an antibody or antibody fragment, "specifically binds" to a target ligand or antigen of interest when it has a significantly higher binding affinity for, and consequently is capable of distinguishing, that target ligand or antigen, compared to its affinity for other unrelated proteins, under similar binding assay conditions. Typically, an antigen binding protein is said to "specifically bind" its target antigen when the dissociation constant ($K_D$) is $10^{-8}$ M or lower. The antigen binding protein specifically binds antigen with "high affinity" when the $K_D$ is $10^{-9}$ M or lower, and with "very high affinity" when the $K_D$ is $10^{-10}$ M or lower.

"Antigen binding region" or "antigen binding site" means a portion of a protein that specifically binds a specified target ligand or antigen. For example, that portion of an antigen binding protein that contains the amino acid residues that interact with a target ligand or an antigen and confer on the antigen binding protein its specificity and affinity for the antigen is referred to as "antigen binding region." In an antibody, an antigen binding region typically includes one or more "complementary binding regions" ("CDRs"). Certain antigen binding regions also include one or more "framework" regions ("FRs"). A "CDR" is an amino acid sequence that contributes to antigen binding specificity and affinity. "Framework" regions can aid in maintaining the proper conformation of the CDRs to promote binding between the antigen binding region and an antigen. In a traditional antibody, the CDRs are embedded within a framework in the heavy and light chain variable region where they constitute the regions responsible for antigen binding and recognition. A variable region of an immunoglobulin antigen binding protein comprises at least three heavy or light chain CDRs, see, supra (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991, supra; see also Chothia and Lesk, 1987, supra).

The term "target" or "antigen" refers to a molecule or a portion of a molecule capable of being bound by a selective binding agent, such as an antigen binding protein (including, e.g., an antibody or immunologically functional fragment of an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a target molecule that is bound by an antigen binding protein (for example, an antibody or antibody fragment). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antigen binding proteins specific for a particular target will preferentially recognize an epitope on the target in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with proteins of interest, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. By methods known to the skilled artisan, proteins, can be "engineered" or modified for improved target affinity, selectivity, stability, and/or manufacturability before the coding sequence of the "engineered" protein is included in the expression cassette.

The term "derivative," when used in connection with proteins of interest, refers to proteins that are covalently modified by conjugation to therapeutic or diagnostic agents, labeling (e.g., with radionuclides or various enzymes), covalent polymer attachment such as PEGylation (derivatization with polyethylene glycol) and insertion or substitution of natural or non-natural amino acids.

Cloning DNA

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the polypeptide of interest, e.g., antibody sequences.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

Sequencing of DNA is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of genes and cDNAs, one of skill will readily be able to determine, depending on the region sequenced. One source of gene sequence information is the National Center for Biotechnology Information, National Library of Medicine, National Institutes of Health, Bethesda, Md. Gene sequencing can also be done, for example, by standard methods or by so-called "Next-generation" sequencing of engineered DNA constructs prior to transfection. (See, e.g., Buermans, H. P. J., & den Dunnen, J. T., *Next generation sequencing technology: Advances and applications*, Biochimica et Biophysica Acta—Molecular Basis of Disease 1842(10): 1932-1941 (2014)).

Chemical synthesis of parts or the whole of a coding region containing codons reflecting desires protein changes can be cloned into an expression vector by either restriction digest and ligation of 5' and 3' ends of fragments or the entire open reading frame (ORF), containing nucleotide overhangs that are generated by restriction enzyme digestion and which are compatible to the destination vector. The fragments or inserts are typically ligated into the destination vector using a T4 ligase or other common enzyme. Other useful methods are similar to the above except that the cut site for the restriction enzyme is at location different from the recognition sequence. Alternatively, isothermal assembly (i.e., "Gibson Assembly") can be employed, in which nucleotide overhangs are generated during synthesis of fragments or ORFs; digestion by exonucleases is employed. Alternatively, nucleotide overhangs can be ligated ex vivo by a ligase or polymerase or in vivo by intracellular processes.

Alternatively, homologous recombination can be employed, similar to isothermal assembly, except exonuclease activity of T4 DNA ligase can used on both insert and vector and ligation can be performed in vivo.

Another useful cloning method is the so-called "TOPO" method, in which a complete insert containing a 3' adenosine overhang (generated by Taq polymerase) is present, and Topoisomerase I ligates the insert into a TOPO vector.

Another useful cloning method is degenerate or error-prone PCR exploiting degenerate primers and/or a thermally stable low-fidelity polymerase caused by the polymerase within certain reaction conditions. Fragments or inserts are then cloned into an expression vector.

The above are merely examples of known cloning techniques, and the skilled practitioner knows how to employ any other suitable cloning techniques.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the expressed protein by the recombinant host cells); an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Protein Expression

The present high throughput methods for predicting the stability of a protein at low pH or for interrogating the physiochemical properties of a protein of interest typically involves a recombinant protein of interest that is obtained by transfecting a plurality of mammalian host cells. Transfecting can be by transient or stable transfection, e.g., the pooled plasmid constructs (expression vectors) from the cloning step can be transfected into a plurality of host cells (e.g., mammalian, e.g., HEK 293 or CHO, bacterial, insect, yeast cells) for expression using a cationic lipid, polyethylenimine, Lipofectamine™, or ExpiFectamine™, or electroporation. The skilled practitioner is aware of numerous suitable means for transfecting to achieve expression of recombinant antibodies.

The protein of interest is typically obtained by culturing the transfected host cells under physiological conditions allowing the cells to express recombinant proteins, e.g., antibodies or fusion proteins. Most conveniently, the expressed recombinant proteins are directly secreted into the culture supernatant (by employing appropriate secretory-directing signal peptides) and are harvested therefrom; otherwise additional steps will be needed to isolate the expressed antibodies from a cell extract.

For purposes of obtaining the protein(s) of interest used in practicing the present invention, the desired scale of the recombinant expression will be dependent on the type of expression system and the quantity of different proteins or variants to be interrogated. Some expression systems such as ExpiCHO™ usually produce higher yields as compared to some earlier HEK293 technologies. A smaller scale ExpiCHO™ might then suffice as compared to an HEK293 system. Efficiency of transfection can also be a consideration in choosing an appropriate expression system. Electroporation can be a suitable method given its effectiveness, relative low cost and the fact that high-throughput during this step is not critical. Additionally, the ratio of immunoglobulin light chain to heavy chain can be varied during the co-transfection to improve expression of certain variants. The product yield for a given variant has to be sufficient to survive numerous handling steps and produce a signal high enough to be detected by the chosen fluorescence detector.

The transfected host cells are typically cultured by any conventional type of culture, such as batch, fed-batch, intensified fed-batch, or continuous. Suitable continuous cultures included repeated batch, chemostat, turbidostat or perfusion culture. Typically, a viable cell density can be used from $1.0 \times 10^6$ to $2.0 \times 10^7$, or up to about $5 \times 10^7$ cells/mL. It is known that increasing the concentration of cells toward the higher end of the preferred ranges can improve volumetric productivity. Nevertheless, ranges of cell density including any of the above point values as lower or higher ends of a range are envisaged. For purposes of obtaining recombinant protein(s) of interest to be interrogated by the present inventive methods, the desired scale of the recombinant expression and cell culture will be dependent on the type of expression system and the quantity of different proteins of interest to be studied.

Upon culturing the transfected or transformed host cells, the recombinant polypeptide or protein, can be produced intracellularly, in the periplasmic space, or, preferably, directly secreted into the medium. Harvesting the recombinant protein involves separating it from particulate matter that can include host cells, cell aggregates, and/or lysed cell fragments, into a cell-free supernatant fraction that is free of host cells and cellular debris. Such cellular debris is removed, for example, by centrifugation or microfiltration. After the recombinant protein, e.g., recombinant antibodies or fusion protein, is separated from the host cells and/or other particulate debris, harvesting the recombinant protein into a cell-free supernatant fraction can optionally involve capture of the recombinant protein by one or more chromatographic capture steps that can partially purify and/or concentrate the protein, such as Protein A or Protein G or Protein L affinity chromatography. (See, e.g., Frank, M. B., "Antibody Binding to Protein A and Protein G beads" 5. In: Frank, M. B., ed., *Molecular Biology Protocols*. Oklahoma City (1997)).

After harvesting the cell culture fluid comprising a recombinant protein of interest, e.g., an antibody or antibody fragment, can be further purified from the cell-free supernatant fraction. Typically, the purification of recombinant proteins is usually accomplished by an optional series of chromatographic steps such as anion exchange chromatography, cation exchange chromatography, affinity chromatography (using Protein A or Protein G or Protein L as an affinity ligand), hydrophobic interaction chromatography, hydroxy apatite chromatography and size exclusion chromatography. Further, the purification process may comprise one or more ultra-, nano- or diafiltration steps, and/or, optionally, an acidic viral inactivation step. Other optional known techniques for protein purification such as ethanol precipitation, Reverse Phase HPLC, chromatofocusing, SDS-PAGE, and ammonium sulfate precipitation are also possible depending on the protein to be recovered and purified for interrogation by the present inventive methods.

By way of further illustration, the following embodiments of the present invention are enumerated:

Embodiment 1

A method for predicting the stability of a protein at low pH, comprising:
(a) heating to a continuous set of temperatures in the range of about 20° C. to about 95° C. a first reaction mixture comprising a hydrophobic fluorescent dye and a protein of interest, at a first pH value in the range of about pH 4.0 to about pH 4.2, and:
  (i) detecting fluorescence of the dye over the range of temperatures to obtain a first fluorescence curve;
  (ii) obtaining the first derivative of the first fluorescence curve; and
  (iii) determining the temperature transitions of the protein of interest, at the first pH value, from the first derivative of the first fluorescence curve;
(b) heating to a continuous set of temperatures in the range of about 20° C. to about 95° C. one or more second reaction mixture(s) comprising the hydrophobic fluorescent dye and the protein of interest, at one or more different second pH value(s) between about pH 2.9 to about pH 4.0, each different second pH value being lower than the first pH value, and:
  (i) detecting fluorescence of the dye in each of the one or more second reaction mixture(s) over the range of temperatures to obtain a second fluorescence curve for each second reaction mixture;
  (ii) obtaining the first derivative of each second fluorescence curve; and
  (iii) determining the temperature transitions of the protein of interest, at the one or more different second pH value(s), from the first derivative(s) of the second fluorescence curve(s); and
(c) comparing the temperature transition peaks of the protein of interest at the first pH value and at the one or more different second pH value(s), wherein, if a temperature transition peak present at the first pH value is absent or shifted at one or more of the different second pH value(s), the protein of interest is predicted to display poor stability at low pH.

Embodiment 2

The method of Embodiment 1, wherein determining the temperature transitions of the protein of interest from the first derivative of the first fluorescence curve or from the first derivative of each second fluorescence curve, or both, comprises:
(a) locating on the first derivative of the first fluorescence curve a lowest temperature peak (the $T_1$ peak of the first fluorescence curve) having a maximum intensity of at least about 30% of the maximum intensity peak of the first derivative of the fluorescence curve, wherein the fluorescence intensity of the $T_1$ peak of the first fluorescence curve is IT), and the temperature at which the maximum IT) occurs is $T_{T1}$ of the first fluorescence curve; and
(b) for each of the one or more second fluorescence curve(s), finding a peak closest in temperature to the:
  (i) $T_{T1}$ of the first fluorescence curve; or
  (ii) $T_{T1}$ of a different second fluorescence curve obtained from a different second reaction mixture with a different pH value closest to its pH value; and designating that peak the $T_1$ peak of the second fluorescence curve, wherein the fluorescence intensity of the $T_1$ peak of each second fluorescence curve is the $I_{T1}$ of the second fluorescence curve and the temperature at which the maximum $I_{T1}$ of the second fluorescence curve occurs is the $T_{T1}$ of the second fluorescence curve;
(c) calculating the fluorescence intensity value (I) of all points of the first derivative of each of the first fluorescence curve and the one or more second fluorescence curve(s) normalized to its $I_{T1}$ ($I_{norm}$), wherein $I_{norm}=I/I_{T1}$;
(d) calculating a relative temperature value ($T_{rel}$) of all points of the first derivative of each fluorescence curve relative to its $T_T$, wherein, $T_{rel}=T-T_{T1}$;
(e) calculating a weight ($W_{WSS}$) of all points of the first derivative of the fluorescence curve, wherein:

$$W_{WSS} = \begin{cases} T_{rel}^2, & \text{if } (T_{rel} > 0 \text{ and } I_{norm} > 0) \\ 0, & \text{otherwise} \end{cases};$$

and
(f) subsequently calculating a scalar weighted shoulder score (WSS), wherein:

$$WSS=\sqrt{I_{norm}W_{WSS}},$$

wherein the position and shape of a second temperature transition ($T_2$) peak and/or a third temperature transition ($T_3$) peak characteristic of the unfolding of the protein of interest are detected as increases in the scalar WSS value.

Embodiment 3

The method of Embodiments 1-2, further comprising:
(g) calculating a weight ($W_{WLS}$) of all points of the first derivative of the first fluorescence curve and of the first derivative of each second fluorescence curve, wherein for all transitions prior to the $T_1$ peak of the first fluorescence curve or prior to the $T_1$ peak of each second fluorescence curve, respectively, $T_{rel}=T_{T1}-T$, and wherein:

$$W_{WLS} = \begin{cases} T_{rel}^2, & \text{if } (T_{rel} > 0 \text{ and } I_{norm} > 0) \\ 0, & \text{otherwise} \end{cases};$$

and
(h) subsequently calculating a scalar weighted leader score (WLS), wherein:

$$WLS=\sqrt{I_{norm}W_{WSS}},$$

wherein the position and shape of any lower temperature transition peak at a $T_{0, -1, -2, etc.}$, less than $T_1$ characteristic of the unfolding of the protein of interest are detected as increases in the scalar WLS value.

Embodiment 4

The method of Embodiments 1-3, wherein the protein of interest is an immunoglobulin.

Embodiment 5

The method of Embodiments 1-4, wherein the protein of interest is a fusion protein.

Embodiment 6

The method of Embodiments 1-5, wherein the method is employed to predict the suitability of the protein of interest for low pH viral inactivation.

Embodiment 7

The method of Embodiments 1-6, wherein the method is employed to interrogate the conformational stability of the protein of interest.

Embodiment 8

The method of Embodiments 1-7, wherein the method is employed to detect Fc glycosylation heterogeneity.

Embodiment 9

A method for interrogating the physiochemical properties of a protein of interest, comprising:
  (a) heating to a continuous set of temperatures, each temperature being a value of T in the range of about 20° C. to about 95° C., a reaction mixture comprising a hydrophobic fluorescent dye and a protein of interest in a buffer, which contains a physiochemical stressor of interest at a reference concentration greater than or equal to zero, and:
    (i) detecting fluorescence of the dye over the range of temperatures to obtain a first fluorescence curve;
    (ii) obtaining the first derivative of the first fluorescence curve; and
  (b) heating to a continuous set of temperatures in the range of about 20° C. to about 95° C. one or more second reaction mixture(s) comprising the hydrophobic fluorescent dye and the protein of interest, at one or more different second concentration value(s) of the physiochemical stressor of interest, each different second concentration value being greater than the reference concentration, and:
    (i) detecting fluorescence of the dye in each of the one or more second reaction mixture(s) over the range of temperatures to obtain a second fluorescence curve for each second reaction mixture; and
    (ii) obtaining the first derivative of each second fluorescence curve;
  (c) determining the temperature transitions of the protein of interest from the first derivative of the first fluorescence curve or from the first derivative of each second fluorescence curve, or both, which comprises:
    (i) locating on the first derivative of the first fluorescence curve a lowest temperature peak (the $T_1$ peak of the first fluorescence curve) having a maximum intensity of at least about 30% of the maximum intensity peak of the first derivative of the fluorescence curve, wherein the fluorescence intensity of the $T_1$ peak of the first fluorescence curve is $I_{T1}$, and the temperature at which the maximum $I_{T1}$ occurs is $T_{T1}$ of the first fluorescence curve; and
    (ii) for each of the one or more second fluorescence curve(s), finding a peak closest in temperature to the:
      (1) $T_{T1}$ of the first fluorescence curve; or
      (2) $T_{T1}$ of a different second fluorescence curve obtained from a different second reaction mixture with a different second concentration value closest to its second concentration value; and designating that peak the $T_1$ peak of the second fluorescence curve, wherein the fluorescence intensity of the $T_1$ peak of each second fluorescence curve is the $I_{T1}$ of the second fluorescence curve and the temperature at which the maximum $I_{T1}$ of the second fluorescence curve occurs is the $T_{T1}$ of the second fluorescence curve;
    (iii) calculating the fluorescence intensity value (I) of all points of the first derivative of each of the first fluorescence curve and the one or more second fluorescence curve(s) normalized to its $I_{T1}$ ($I_{norm}$), wherein $I_{norm}=I/I_{T1}$;
    (iv) calculating a relative temperature value ($T_{rel}$) of all points of the first derivative of each fluorescence curve relative to its $T_{T1}$, wherein, $T_{rel}=T-T_{T1}$;
    (v) calculating a weight ($W_{WSS}$) of all points of the first derivative of the fluorescence curve, wherein:

$$W_{WSS} = \begin{cases} T_{rel}^2, & \text{if } (T_{rel} > 0 \text{ and } I_{norm} > 0) \\ 0, & \text{otherwise} \end{cases};$$

and
    (vi) subsequently calculating a scalar weighted shoulder score (WSS), wherein:

$$\text{WSS} = \sqrt{I_{norm} W_{WSS}},$$

wherein the position and shape of a second temperature transition ($T_2$) peak and/or a third temperature transition ($T_3$) peak characteristic of the unfolding of the protein of interest are detected as increases in the scalar WSS value; and
  (d) comparing the temperature transition peaks of the protein of interest at the reference concentration and at the one or more different second concentration value(s) of the physiochemical stressor of interest, wherein, if a temperature transition peak present at the reference concentration is absent or shifted at one or more of the different second concentration value(s) of the physiochemical stressor of interest, the protein of interest is shown to display poor stability in response to the physiochemical stressor of interest.

Embodiment 10

The method of Embodiment 9, further comprising:
  (e) calculating a weight ($W_{WLS}$) of all points of the first derivative of the first fluorescence curve and of the first derivative of each second fluorescence curve, wherein for all transitions prior to the $T_1$ peak of the first fluorescence curve or prior to the $T_1$ peak of each second fluorescence curve, respectively, $T_{rel}=T_{T1}-T$, and:

$$W_{WLS} = \begin{cases} T_{rel}^2, & \text{if } (T_{rel} > 0 \text{ and } I_{norm} > 0) \\ 0, & \text{otherwise} \end{cases};$$

and
  (f) subsequently calculating a scalar weighted leader score (WLS), wherein:

$$\text{WLS} = \sqrt{I_{norm} W_{WLS}},$$

wherein the position and shape of any lower temperature transition peak at a $T_{0, -1, -2, etc.}$ less than $T_1$ characteristic of the unfolding of the protein of interest are detected as increases in the scalar WLS value.

Embodiment 11

The method of Embodiments 9-10, wherein the protein of interest is an immunoglobulin.

Embodiment 12

The method of Embodiments 9-11, wherein the protein of interest is a fusion protein.

Embodiment 13

The method of Embodiments 9-12, wherein the physiochemical property of the protein of interest is stability at low pH.

Embodiment 14

The method of Embodiments 9-13, wherein the physiochemical property of the protein of interest is conformational stability.

Embodiment 15

The method of Embodiments 9-14, wherein the method is employed to detect Fc glycosylation heterogeneity.

Embodiment 16

The method of Embodiments 9-15, wherein the physiochemical property of the protein of interest is thermal stability.

Embodiment 17

The method of Embodiments 9-16, wherein the physiochemical property of the protein of interest is ANS dye binding to evaluate extrinsic fluorescence binding.

Embodiment 18

The method of Embodiments 9-17, wherein the physiochemical property of the protein of interest is measurement and interpretation curves of intrinsic fluorescence.

The following working examples are illustrative and not to be construed in any way as limiting the scope of the invention.

EXAMPLES

Example 1. Materials and Methods

Proteins.

Purified monoclonal antibodies (mAbs) and fusion proteins were produced using industry standard recombinant mammalian expression systems (for transient or stable expression) and purification processes. Purified mAb drug substance was either diluted directly into an experimental buffer system or buffer exchanged and concentrated to a set concentration to ensure a final target pH. Protein concentrations were adjusted to the final target concentration by diluting with the experimental buffer. The water used in making all buffers was purified by a Milli-Q® (Millipore Corporation) water purification system, which includes an ion exchange cartridge. The purity of the water was monitored by measuring the conductivity, with a value greater than 18.2 MΩcm-1 (@ 25 Â° C.) being acceptable. All buffers and other ingredients used for the preparation of experimental buffers were USP grade or equivalent. The Sypro® Orange Dye (5000× in DMSO) was purchased from Invitrogen. The PCR plates and plate sealing foils were purchased from Roche.

Buffer Preparation.

100 mM Acetate. pH 3.6.

Sodium acetate (0.58 g/L) and glacial acetic acid (5.31 g/L) were blended with Milli-Q® water to a 1 liter final volume. The pH was verified to be 3.6±0.1.

DSF Low pH Buffer Preparation.

Twelve DSF low pH buffers were prepared in 0.1 pH increments and range in pH from 3.0 to 4.1. Each low pH buffer was prepared from a starting solution of 100 mM acetate, pH 3.6. Buffers below pH 3.6 were prepared by adjusting the pH down with 2 M acetic acid and those above pH 3.6 were adjusted with 2 M tris base. All pH adjusted buffer solutions were filtered through a 0.2 μm filter unit prior to use in the DSF low pH screen assay.

Differential Scanning Fluorimetry.

Differential Scanning Fluorimetry (DSF) was performed on a Roche Light Cycler 480 II system. Protein test samples were diluted to 0.2-0.3 mg/mL into a specific buffer. The diluted protein was blended in equal volumes with a dilute Sypro® Orange solution in a microtiter sample plate. The sample plate was centrifuged and then placed into the Roche Light Cycler 480 II system for analysis. The sample plate was equilibrated to 20° C. for 15 seconds followed by a thermal ramp to 95° C. using a 0.06° C./second ramp rate. Sypro® Orange was detected at an excitation of 465 nm and an emission of 580 nm. A continuous acquisition mode was used with data acquired at 10/° C.

Differential Scanning Fluorimetry Low DH Screen Method.

Differential Scanning Fluorimetry (DSF) was performed on a Roche Light Cycler 480 II system. The Sypro® Orange was diluted to a 60× stock solution using Milli-Q® water as a diluent. The 60× stock solution was then diluted into each of the 12 DSF acetate buffers (pH from 3.0-4.1), to achieve a final Sypro® Orange concentration of 5× to 6×. The test proteins were diluted into each of the 12 DSF acetate buffers, ranging in pH 3.0-4.1, to a final protein concentration of 0.2-0.3 mg/mL. Using a 12 channel multichannel pipette, the 12 dilute protein preparations (pH 3.0-4.1) were blended 1:1 with the 12 dilute Sypro® Orange solutions. The microtiter plate was sealed, incubated at room temperature for either 30 minutes. The sample plate was centrifuged and then placed into the Roche Light Cycler 480 II system for analysis. The Light Cycler was programmed to equilibrate the samples to 20° C. and then ramp up to 95° C. with a ramp rate of 0.06° C. second. The Sypro® Orange was detected using an excitation of 465 nm and an emission of 580 nm. Data was acquired at 10 acquisitions/° C.

Size Exclusion Chromatography.

Size exclusion (SE)-HPLC analysis was performed using a Waters XBridge Protein BEH SEC 200 A. Separation was achieved under native conditions using a phosphate, sodium chloride running buffer. Peak elution was detected by UV absorbance, and the integrated purity results were reported as relative peak area percentages of the high molecular weight (HMW) component, main component (monomer), and low molecular weight (LMW) component, relative to total corrected area.

Bench Scale Low pH Hold Stability.

A bench scale study was conducted to evaluate the hold stability of molecules at low pH, to determine the operating range for low pH viral inactivation. Each test protein was diluted with a pre-determined volume of 1 M acetic acid to reach a target pH of 3.2, 3.3, 3.4, or 3.5. Samples were held for durations of time between 2 and 60 minutes. After the low pH hold, the samples were neutralized with a predetermined volume of 1 M tris base. The neutralized pools were assessed by size exclusion chromatography to quantify the level of high molecular weight species relative to a control sample.

High Throughput Low pH Screen by SE-HPLC.

The low pH screen method was developed to determine the solution stability of a protein at low pH evaluating the level of high molecular weight (HMW) in a sample after a brief hold at low pH conditions. The pH of 100 μL of a 1 mg/mL protein solution in 20 mM sodium phosphate, 150 mM sodium chloride, pH 7.2 (PBS) was adjusted to pH 3.3 with 2 M acetic acid. The protein solution was held for 30 minutes at room temperature and then neutralized to pH 5.0 with 2 M tris-base. A control sample, without pH adjustment, was prepared in parallel using PBS in place of the acid and base additions. The HMW levels of the protein solutions were determined by SE-HPLC.

Mass Spectrometry based Multi-attribute Method (MAM).

Samples were denatured with >5 M guanidine, reduced with 10 mM dithiothreitol (DTT), and alkylated with 20 mM iodoacetic acid. Excess reagents were removed by size-exclusion based desalting columns. Trypsin was added at a 1:10 enzyme to substrate ratio and samples were digested for 30 minutes at 37° C. The resulting peptides were separated by RP-HPLC with a formic acid/acetonitrile (FA/ACN) gradient over a C18 column and monitored by mass spectrometry detection using a Thermo Fisher Q-Exactive Mass Spectrometer. Identification and relative quantification of the individual peptides was performed using Genedata's Expressionist software (Rogers, R S et al., *Development of a quantitative mass spectrometry multi-attribute method for characterization, quality control testing and disposition of biologics*, MAbs 7(5):881-90 (2015)).

Self Interaction Nanoparticle Spectroscopy (SINS).

The SINS assay utilizes gold colloid surfaces to measure protein-protein interaction, performed according to the method of Liu et al. (Liu, Y et al., *High-throughput screening for developability during early-stage antibody discovery using self-interaction nanoparticle spectroscopy*, mAbs 6:2: 438-492 (2014)). Gold colloids have unique optical absorption properties dependent on their aggregation state, absorbing light at longer wavelengths as nanoparticle aggregation occurs. Protein self-interaction is assessed by capturing test antibodies on the surface of a gold colloid and measuring the shift of the absorbance maxima. If the immobilized antibodies self-interact, the absorbance maximum of the spectrum red shifts to longer wavelengths, or blue shifts to shorter wavelengths if less interaction occurs.

Chemical Unfolding Assay.

Chemical unfolding assay utilizes chemical denaturants such as guanidine hydrochloride or urea to fully denature a protein or antibody. The unfolding can be monitored by several techniques including intrinsic fluorescence, circular dichroism, and UV absorption. By increasing the concentration of the denaturant, the measured output follows a sigmoidal relationship from a fully folded to a fully unfolded state, typically following a two-state model. From these unfolding curves, an assessment of the protein stability can be obtained by calculating the change in the Gibbs free energy of unfolding, $\Delta G$, and the inflection point, $C1/2$, of the unfolding curve. Theoretically, the greater the $\Delta G$ and $C1/2$, the more structurally or conformationally stable the molecule. (See, e.g., J. M. Scholtz, J M et al., *Chapter 23 Solvent Denaturation of Proteins and Interpretations of the m Value*. Methods Enzymol. 466:549-565 (2009); Freire, E et al., *Chemical denaturation as a tool in the formulation optimization of biologics*, Drug Discov. Today. 18:1007-1013 (2013); Pace, C N, *Determination and Analysis of Urea and Guanidine Hydrochloride Denautration Curves*, Metho. 131 (1986) 266-280 (1986); Eftink, M R, *Use of multiple spectroscopic methods to monitor equilibrium unfolding of proteins*, Methods Enzymol. 259 (1995) 487-512 (1995)).

Example 2. High Throughput DSF pH Screen to Predict Viral Inactivation Solution Protein Stability A series of protein molecules including monoclonal antibodies and a fusion protein were analyzed by the inventive high throughput method for predicting the stability of a protein at low pH, employing DSF, and by a bench scale low pH hold stability study. The molecules used for this analysis are shown in Table 1, below, designated by arbitrary Protein Numbers.

TABLE 1

Protein molecules analyzed by DSF pH screening assay.

| Protein Number | Molecule Type |
| --- | --- |
| Protein 1 | mAb (IgG1) |
| Protein 2 | Fusion Protein (Fc-containing) |
| Protein 3 | mAb (IgG1) |
| Protein 4 | mAb (IgG4) |
| Protein 5 | mAb (IgG1) |
| Protein 6 | mAb (IgG1) |

Bench Scale Low pH Hold Stability.

The first five of the proteins listed in Table 1 were evaluated by a bench scale low pH hold stability study. Protein 6 from Table 1 was not tested by this technique due to its known pH instabilities at pH 3.7 and below. The five molecules were titrated down to a target pH and then held for a set duration of time before they were neutralized. Hold times of 2, 4, 8, 15, 30, and 60 minutes were tested. The high molecular weight levels of the neutralized samples were assessed by size exclusion chromatography to assess the aggregation levels after low pH hold. Results from the 2 and 60 minute timepoints are summarized in Table 2, below.

Regardless of hold pH, Proteins 1, 2 and 3 had no change in percent high molecular weight (% HMW) after the 60 minutes hold when compared to the control sample. These three molecules were very stable under low pH conditions and would thus fit into typical platform downstream manufacturing processes. Protein 4 had an increase in % HMW after 60 minutes at pH 3.2 and pH 3.3 but had unchanged levels of HMW at the pH 3.4 and 3.5 conditions. Protein purification unit operations, including the viral inactivation step, are typically conducted at pH 3.4 and above and therefore this molecule is considered to have acceptable low pH stability and would likely fit into most downstream platform processes. Regardless of pH, Protein 5 had an immediate increase in % HMW, when compared to the control sample, when held for 2 minutes at all pH conditions. Significant increases in % HMW were evident after 60 minutes at pH 3.2 and 3.3. The increase of HMW at all pH conditions indicate this molecule is very susceptible to aggregate formation under low pH conditions, suggesting this protein would be difficult to manufacture under industry standard platform operating conditions.

Out of the five molecules tested, three were very stable with little to no impact in aggregation levels when held at low pH. Two molecules (Protein 4 and Protein 5) had increases of high molecular weight under the lowest pH conditions with Protein 5 having evidence of aggregation at all pH conditions.

TABLE 2

Aggregate formation (% HMW) results determined by size exclusion chromatography.

| Protein Sample | Hold Time (minutes) | Control | Target Hold pH | | | |
|---|---|---|---|---|---|---|
| | | | 3.2 | 3.3 | 3.4 | 3.5 |
| Protein 1 | 2 | 0.2% | 0.1% | 0.2% | 0.2% | 0.2% |
| | 60 | | 0.2% | 0.2% | 0.2% | 0.2% |
| Protein 2 | 2 | 2.7% | 2.4% | 2.5% | 2.5% | 2.6% |
| | 60 | | 2.7% | 2.5% | 2.4% | 2.6% |
| Protein 3 | 2 | 0.7% | 1.4% | 0.7% | 0.7% | 0.7% |
| | 60 | | 0.6% | 0.7% | 0.7% | 0.7% |
| Protein 4 | 2 | 2.9% | 3.8% | 3.0% | 2.9% | 2.9% |
| | 60 | | 28.6% | 6.3% | 3.2% | 2.9% |
| Protein 5 | 2 | 5.6% | 7.8% | 7.6% | 7.2% | 6.8% |
| | 60 | | 19.2% | 10.5% | 7.9% | 7.6% |

Differential Scanning Fluorimetry pH Screen Results.

The six molecules outlined in Table 1 were analyzed by the inventive method for interrogating the physiochemical properties of a protein of interest, in particular for predicting the stability of a protein at low pH (i.e., high $H^+/H_3O^+$ concentration as physiochemical stressor), employing DSF. The raw fluorescent curves from the DSF pH screen assay were exported and data analysis was performed to calculate WSS and WLS values using the algorithm described herein. To visually assess the data, the first derivatives were plotted as a series of stacked curves as illustrated for Protein 5 in FIG. 1. The algorithm tracks each peak as the transition temperatures shift due to pH changes. The Protein 5 first derivative curve shown in FIG. 1 had two transitions. At pH 3.2 the T1 transition was no longer evident in the profile. Each transition represents the temperature at which that structural domain or domains, begins to unfold, exposing hydrophobic regions which allows Sypro® Orange dye binding. The loss of the T1 signal indicates the dissociation of Sypro® Orange from the protein due to a loss in structure (He, F et al., *High Throughput thermostability screening of monoclonal antibody formulations*, J. Pharm. Sci. 99 (4): 1707-1720 (2010)). The automatically generated stacked plots provide a means to qualitatively interrogate the physiochemical properties of a protein and its thermal stability as it relates to decreasing pH conditions, or to another physiochemical stressor.

Figure 2:
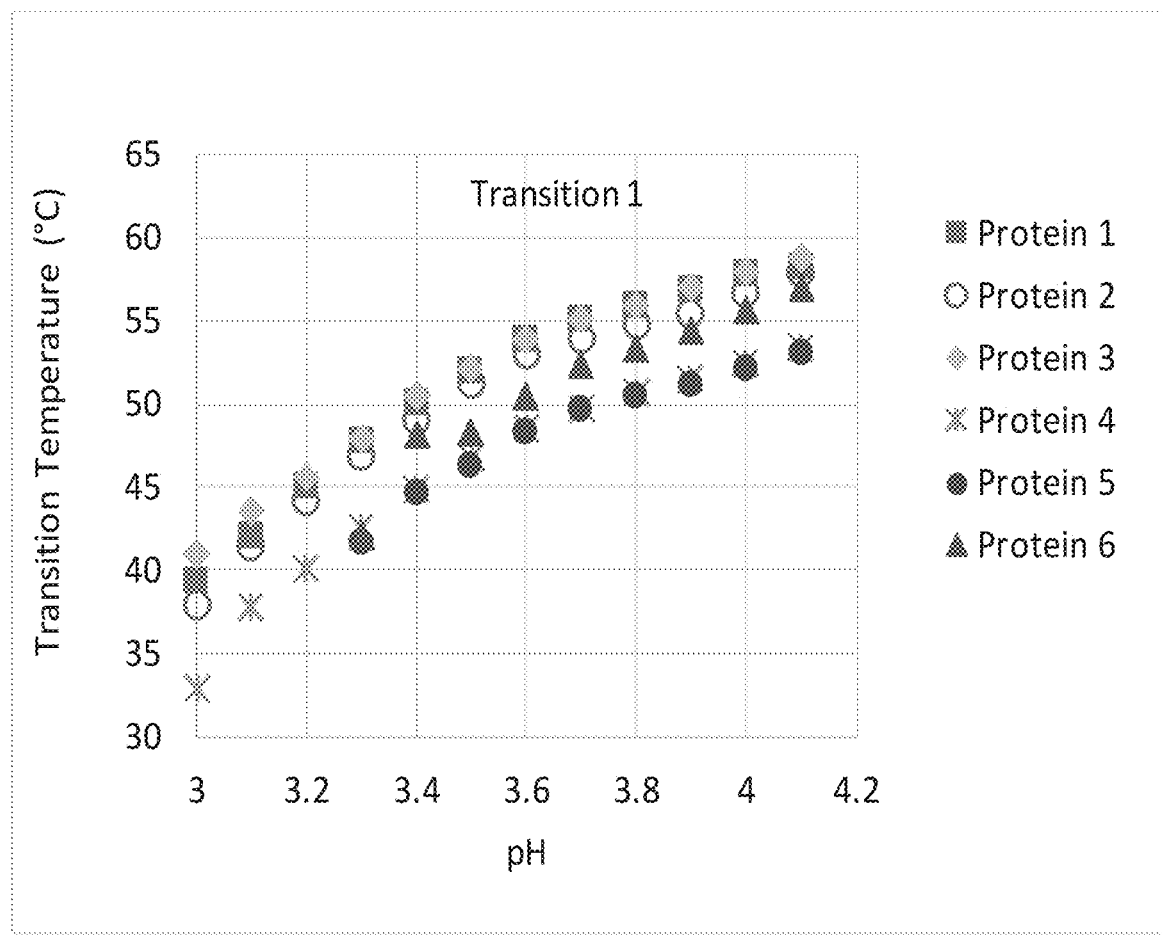
FIG. 2 shows a summary of the Transition 1 temperatures (T1) from six different example proteins. Proteins 5 and 6 demonstrated absent transitions under low pH conditions suggesting protein unfolding or aggregation events.
Figure 3:
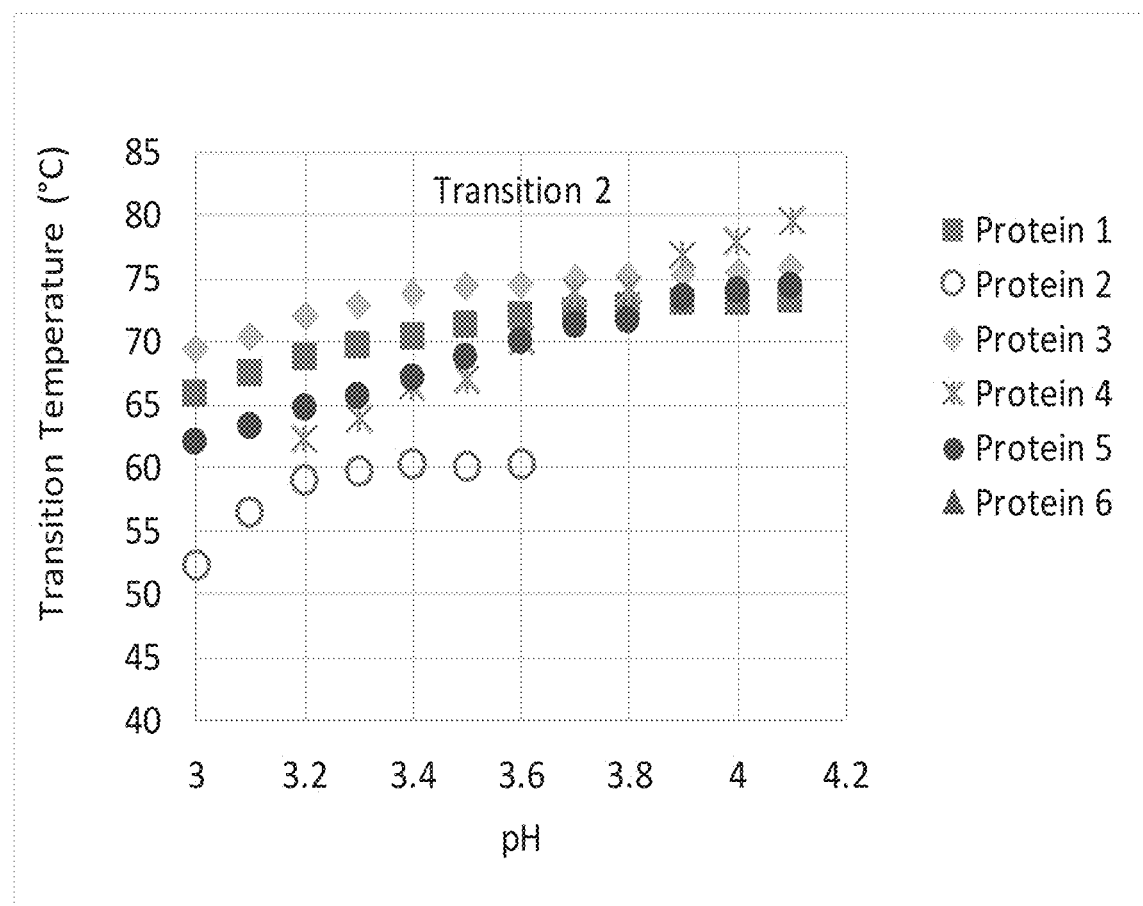
FIG. 3 show a summary of the transition 2 temperatures (T2) from six example proteins. Protein 2, a fusion protein, had one transition of 58° C. when tested at pH 4.1, however as the pH was decreased an additional transition appeared, probably due to a decrease in CH2 stability at low pH revealing other unfolding events. Protein 4 had a loss of fluorescence signal under pH 3.0 and 3.1 conditions. Protein 6 lost all evidence of a second transition suggesting that a domain had unfolded or that an aggregation event occurred.

A summary of the transition temperature results from the six test molecules are shown in Table 3, and the data are graphically represented in FIG. 2 and FIG. 3. Transition temperatures at the pH 4.1 conditions were higher than at pH 3.0, indicating higher temperatures are required to unfold a molecule in a pH 4.1 buffer versus a pH 3.0 buffer. Five of the test molecules shown in Table 3 were IgGs, proteins with defined CH2, CH3 and Fab structural domains. The sixth molecule, Protein 2, is a Fc-fusion protein and does not have a Fab domain. The unfolding of each domain was monitored by Sypro® Orange binding to hydrophobic pockets exposed during thermal ramping, regions of the molecule previously inaccessible when in their native state. The CH2 domain is known to be more pH sensitive than the Fab domain (see, e.g., Kameoka, D et al., *Effect of buffer species on the unfolding and the aggregation of humanized IgG*, J. Biochem. 142:383-391 (2007); Vermeer, A W et al., *The thermal stability of immunoglobulin: Unfolding and aggregation of a multi-domain protein*, Biophys. J. 78:394-404 (2000)). Therefore, Transition 1 (T1) is likely the CH2 domain. For the majority of IgGs with two transitions, the Transition 2 (T2) represents the thermal stability of both the CH3 and Fab domain. This observation was confirmed in our laboratory by studies in which sequence optimized Fab domains have resulted in an unchanged T1 (CH2 domain) but with shifting T2 and occasionally the appearance of a third unfolding event at a higher temperature, presumably the Fab or CH3 domain, when compared to the native sequence (data not shown).

Discussion of Transition 1.

As shown in Table 1, Proteins 1, 2 and 3 had T1 transitions at all pH conditions. Proteins 5 and 6 had no detectable transitions at pH 3.0-3.2, indicating the loss of structure under those pH conditions and stability issues under low pH conditions.

Discussion of Transition 2.

Proteins 1, 3 and 5 had second transitions (T2s) for all pH conditions, indicating very pH stable CH3 and Fab domains. Protein 4 was missing T2s at pH 3.0 and 3.1, implying that this molecule may have pH sensitivities for long hold times at these low pH conditions.

Protein 6 had no evident T2 peak when run under these experimental conditions. Early method development experiments using only a 5 minute hold after protein and Sypro® Orange blending determined that Protein 6 has a T2, however, when held for 30 minutes, the pH sensitive domains (Fab and/or CH3 domains) unfold or aggregate, resulting in complete loss of Sypro® Orange fluorescent signal.

Protein 2 had no T2 between pH 3.7-4.1, however a second transition became evident at pH 3.6 and lower pH conditions. Protein 2 is a Fc-fusion protein which results in a slightly different profile from the IgGs examples. For fusion proteins and some IgGs, the protein's structural domains have similar hydrophobic patterns during thermal ramping, resulting in only one apparent transition at the pH 4.1 condition. As the protein is tested in lower pH buffer conditions, the pH sensitive CH2 domain has reduced thermal stability, as evident by subsequently decreasing transition temperatures as a function of pH. This shift in CH2 transition temperature allows the resolution of other structural domains, resulting in the appearance of a second transition as the pH is decreases. Therefore, at pH 3.6, Protein 2 exhibited the appearance of a second transition, likely the CH3 domain, a structure that is sustained down to pH 3.0. These data predict that the Fc-fusion Protein 2 molecule is very stable at low pH, for example, as would be encountered during a viral inactivation step in manufacturing.

In all cases, the data obtained from the inventive high throughput DSF pH screen, as described above, correlate well with the foregoing bench scale low pH stability results. DSF does not directly measure or detect aggregation, but rather monitors the changes in Sypro® Orange binding due to loss of tertiary structure or from protein aggregation events. Therefore, we do not expect the DSF result at a particular pH to match identically with the bench scale data. Rather, we anticipate the DSF results will inform molecular design activities to identify molecules that have pH sensitivities evident by the loss of transitions during low pH titrations. Molecules, with a single transitions during low pH titration, are significantly less pH stable than molecules with two transitions. In all cases, molecules with two transitions maintained during the pH 4.1-3.0 titration are very pH stable, results confirmed by the bench scale low pH hold study. Molecules with T1 and/or T2 transition losses upon low pH exposure have differing degrees of pH instabilities as indicated by the bench scale model.

TABLE 3

Summary of the DSF pH Screen Protein Transition 1 and Transition 2 Temperatures (° C.)

| | Protein Sample | Buffer pH | | | | | | | | | | |
|---|---|---|---|---|---|---|---|---|---|---|---|---|
| | | 3.0 | 3.1 | 3.2 | 3.3 | 3.4 | 3.5 | 3.6 | 3.7 | 3.8 | 3.9 | 4.0 | 4.1 |
| Transition 1 | Protein 1 | 39.4 | 42.1 | 45.0 | 47.8 | 50.0 | 52.0 | 53.8 | 55.1 | 56.0 | 56.9 | 57.8 | 58.3 |
| | Protein 2 | 37.9 | 41.4 | 44.2 | 46.9 | 49.1 | 51.2 | 53.0 | 54.0 | 54.7 | 55.5 | 56.7 | 57.9 |
| | Protein 3 | 41.0 | 43.5 | 45.6 | 47.9 | 50.4 | 52.1 | 54.0 | 55.1 | 56.0 | 57.0 | 58.0 | 58.8 |
| | Protein 4 | 32.9 | 37.8 | 40.1 | 42.5 | 44.9 | 46.8 | 48.5 | 49.7 | 50.7 | 51.5 | 52.5 | 53.4 |
| | Protein 5 | ND | ND | ND | 41.7 | 44.6 | 46.3 | 48.3 | 49.6 | 50.5 | 51.2 | 52.1 | 53.0 |
| | Protein 6 | ND | ND | ND | 42.1 | 48.1 | 48.3 | 50.5 | 52.4 | 53.4 | 54.5 | 55.7 | 57.1 |
| Transition 2 | Protein 1 | 65.8 | 67.5 | 68.7 | 69.6 | 70.5 | 71.3 | 72.0 | 72.5 | 72.9 | 73.1 | 73.1 | 73.4 |
| | Protein 2 | 52.2 | 56.6 | 59.0 | 59.7 | 60.4 | 60.1 | 60.3 | ND | ND | ND | ND | ND |
| | Protein 3 | 69.6 | 70.4 | 72.0 | 72.9 | 73.9 | 74.4 | 74.5 | 74.9 | 75.1 | 75.3 | 75.6 | 75.8 |
| | Protein 4 | ND | ND | 62.3 | 64.0 | 66.4 | 67.0 | 70.2 | 74.0 | 74.1 | 76.9 | 77.9 | 79.5 |
| | Protein 5 | 62.0 | 63.4 | 64.8 | 65.8 | 67.1 | 68.7 | 70.0 | 71.2 | 71.7 | 73.4 | 74.1 | 74.3 |
| | Protein 6 | ND | ND | ND | ND | ND | ND | ND | ND | ND | ND | ND | ND |

ND = transition was not detected

Example 3. High Throughput DSF pH Screen Method Detecting Glycan Difference-Related Effects During process development of a monoclonal antibody, two variants of a protein with the same amino acid sequence, designated Protein "A" and Protein "B," were generated with differing levels of Fc-glycans, as confirmed by multi-attribute method (MAM; method described in Example 1 hereinabove) peptide map analysis. The DSF pH screen analysis was performed on these two samples using a pH range of 3.0-4.1.

Multi-Attribute method (MAM)—Fc-Glycan Analysis.

The amino acid sequence of the two samples was confirmed to be identical however the two samples had differing levels of glycans. A summary of the major glycan species is summarized in Table 4. Two N-glycan structures fucosylation and terminal B-galactose are known to impact a protein's structure. (See, e.g., Raju, T S, *Terminal sugars of Fc glycans influence antibody effector functions of IgGs*, Current Opinion in Imm. 20(4):471-478 (2008); Krapp, S et al., *Structural Analysis of Human IgG-Fc Glycoforms Reveals a Correlation Between Glycosylation and Structural Integrity*, J. Mol. Biol. 325(5):979-989 (2003); Ferrara, C et al., *Unique carbohydrate-carbohydrate interactions are required for high affinity binding between RcγRIII and antibodies lacking core fucose*, Proc. Natl. Acad. Sci. USA 108(31):12669-12674 (2011)).

The total fucosylation levels was 16.7% lower and the level of terminal B-Galactose was 25.5% higher in Protein "A" compared with Protein "B." (See, Table 4, below).

TABLE 4

Major Fc-Glycan species as detected by MAM

| Fc-Glycan Species | Protein "A" | Protein "B" |
|---|---|---|
| % A1G0F | 0.5 | 11.3 |
| % A2G0 | 25.9 | 0.9 |
| % A2G0F | 38.4 | 60.2 |
| % A2G1 | 9.9 | 0.4 |
| % A2G1F | 19.4 | 3.4 |
| % High Mannose | 1.0 | 19.3 |
| Total Fucosylation | 58.2 | 74.9 |
| Total Terminal B-Galactose | 29.3 | 3.8 |

High Throughput DSF pH Screen Results.

Figure 4A:
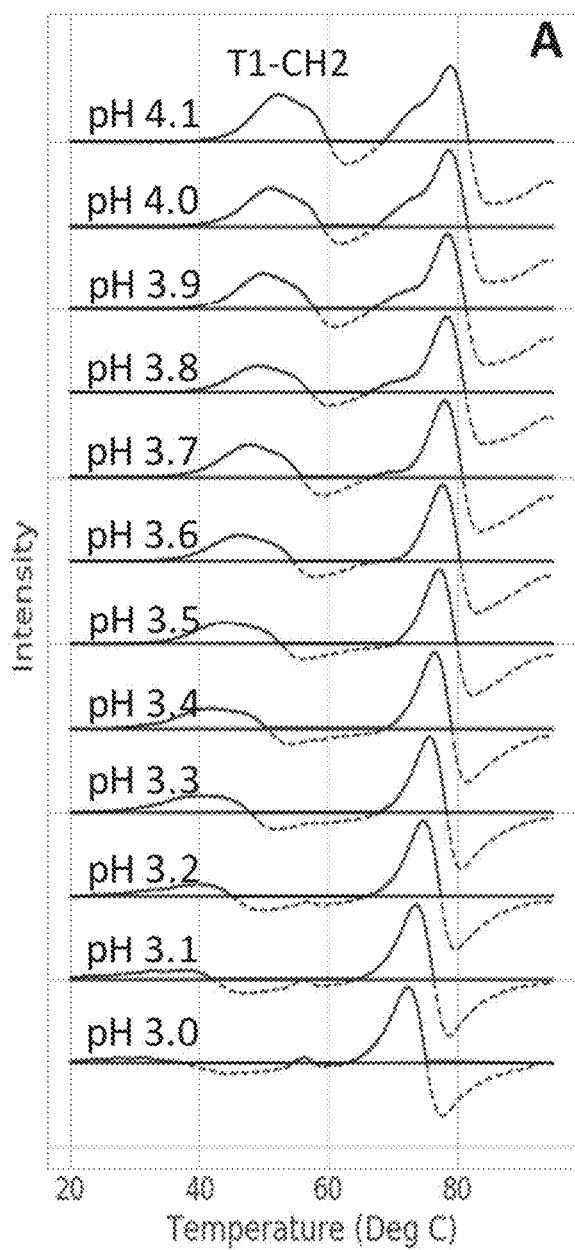
FIG. 4A-B shows representative stacked plots of the DSF pH screen results for Protein "A" (FIG. 4A) and Protein "B" (FIG. 4B) at various pH values. A heterogeneity of the CH2 domain was evident in Protein "A" compared to Protein "B." Known differences in Fc-glycans moieties between these two samples are implicated in these profile differences.
Figure 4B:
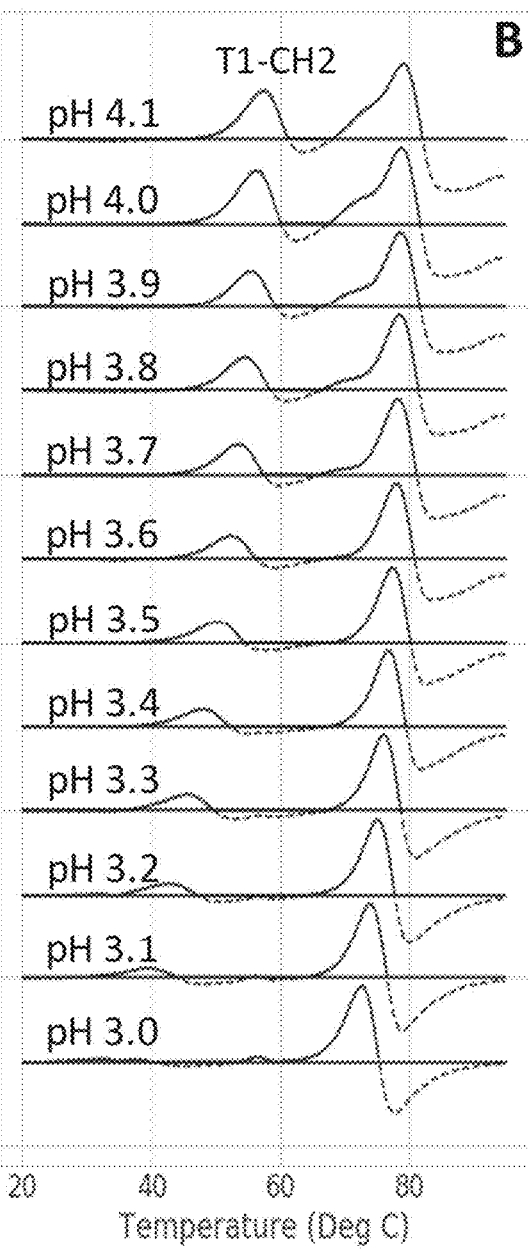

The inventive method for predicting the stability of a protein at low pH, employing DSF, was used to interrogate the physiochemical properties of Protein "A" and Protein "B." A stacked plot from this DSF pH screen analysis are shown in FIG. 4. During DSF analysis thermal ramping of the samples from 25-95° C. showed differences in the transition 1 peak, labeled as T1-CH2. At pH 4.1, two major peaks were evident in the profile. Protein "A" has a discernable doublet in the T1-CH2 transition peak implying there is a secondary structural variant resulting in slight difference in thermal unfolding. Extensive DSF studies studying mAb variant analysis indicate this peak represents the thermal unfolding event of the CH2 domain, the region of the molecule that contains the Fc-glycan species. The remaining peaks in the profile were identical between the two samples, indicting similar structure in other regions of the molecule.

Deuterium exchange results by Houde et al. indicate that terminal galactosylation has an impact of the CH2 domain structure, and they further conclude that fucosylation level is not sufficient to alter the structure. (Houde, D et al., *Characterization of IgG1 conformation and conformational dynamics by hydrogen/deuterium exchange mass spectrometry*, Anal. Chem. 81(7):2644-2651 (2009)). DSF work conducted by Alsenaidy et al. evaluated the physical stability of di-glycosylated, mono-glycosylated and non-glycosylated IgG1-Fc proteins at pH 4.0, 4.5, 5.0, 5.5 and 6.0 conditions. (Alsenaidy, M A et al., *Physical stability comparisons of IgG1-Fc variants: effects of N-glycosylation site occupancy and Asp/Gln residues at site Asn 297*, J. Pharm. Sci. 103(6): 1613-1627 (2014)). In their case, raw fluorescence intensity Sypro® Orange plots were utilized to evaluate Fc proteins and suggested glycosylated Fc proteins are more stable than mono or non-glycosylated proteins. Our data indicate the DSF pH screen and data analysis tools are capable of detecting structural differences due to Fc-glycan differences previously not detected by orthogonal biochemical and biophysical techniques. Given the equivalent amino acid sequence of the two samples, we surmise the detected differences are due to structural variants resulting from differences in the Fc-glycan structures. Further studies, utilizing enzymatic digestion can be used to investigate the relationship between Fc N-glycan species and protein structure as detected by the DSF pH screening assay.

Example 4. High Throughput DSF Screening Method Used to Detect Other Structural Differences The inventive high throughput method for predicting the stability of a protein at low pH, involving DSF, was used to interrogate other physiochemical properties of another protein of interest. A monoclonal antibody, designated "mAb1", and two mAb1 amino acid sequence variants, mAb1-V1 and mAb1-V2, were evaluated by a battery of biochemical and biophysical techniques to screen these molecular entities for solution stability properties in an effort predict product manufacturability and fit to a protein processing platform. The biochemical and biophysical techniques included purity assessment by size exclusion chromatography (SE-HPLC), self-induced nanoparticle spectroscopy (SINS), intrinsic fluorescence with guanidine chemical unfolding, and a single point DSF analysis in phosphate buffered saline. The results from those screening tests indicate the two sequence variants had significantly improved solution stability and thermal stability when compared to the parent molecule, however the two variants had virtually indistinguishable data profiles from each other, implying the molecules had equivalent thermodynamic stability.

The three molecules, mAb1, mAb1-V1, and mAb1-V2 were assessed by the high throughput low pH screen assay (with SE-HPLC) and the DSF screening method to further interrogate these molecules for differences.

High Throughput Low DH Screen Assay Results.

The mAb1 parental sample and the two sequence variants mAb1-V1 and mAb1-V2 were titrated down to pH 3.3 with a known volume of 1 M acetic acid, held for 30 minutes and then neutralized to pH 5.2. Size exclusion analysis of the pH titrated sample compared against a non pH-shifted control sample was conducted and a summary is shown in Table 5, below. The parent molecule mAb1 had a 32.2% increase in high molecular weight after the 30 minute hold while the two sequence variants had less % HMW after the low pH hold, compared to control samples. The reduction of high molecular weight levels after low pH hold is likely due to partial unfolding of the protein, followed by protein refolding into a monomer like conformation once the pH was returned to a favorable level. The two mAb1 sequence variants had similar levels of HMW after the low pH hold study.

TABLE 5

Aggregation (% HMW) determined by SE-HPLC ("Control") or High Throughput DSF Screen (right column).

| | % HMW Control | % HMW pH 3.3 |
|---|---|---|
| mAb1 - Parent | 7.6 | 39.8 |
| mAb1-V1 | 5.4 | 2.9 |
| mAb1-V2 | 6.1 | 3.6 |

A summary of the DSF pH screen first derivative stacked plots are shown in FIG. 7A-C. The mAb1 (parent) molecule had a single transition throughout the pH titration experiment while the two variants each had two transitions (See, FIG. 7A-C). Molecules with only one unfolding transition during DSF low pH screen testing consistently have lower thermal stability. As shown by the % HMW levels in Table 5, those molecules have aggregation problems during low pH hold studies. When tested by the DSF low pH screen assay, the two mAb1 sequence variant molecules had increased thermal stability (higher transition temperatures) when compared to the mAb1 parent molecule and we see a corresponding improvement in the % HMW levels after low pH hold (Table 5).

Table 6, below, summarizes the T2 temperatures for the two mAb1 sequence variants, mAb1-V1 and mAb1-V2. The mAb1-V1 protein had a significantly higher T2 peak than the mAb1-V2 variant, indicating that this sequence modification improves that structural domain's thermal stability. Interestingly, the mAb1-V1 T2 values during low pH titration from pH 4.1 to 3.0, only decreased by 6.1° C. as opposed to a 17° C. decrease for the mAb1-V2 sample. This dramatic difference in thermal stability indicates the mAb1-V1 sequence variant is more resistant to unfolding when subjected to pH and temperature stressors. In this example, the DSF pH screen technique can detect structural differences between the two sequence variants that were previously unresolved by other biophysical and biochemical analyses conducted during molecular screening.

TABLE 6

High Throughput DSF pH screening results showing Transition 2 (T2) for mAb1-V1 and mAb1-V2 variants.

| | T2 Temperature (° C.) | |
|---|---|---|
| pH | mAb1-V1 | mAb1-V2 |
| 4.1 | 78.1 | 64.9 |
| 4 | 77.7 | 64.0 |
| 3.9 | 77.5 | 63.2 |
| 3.8 | 77.6 | 62.4 |
| 3.7 | 77.4 | 61.4 |
| 3.6 | 76.8 | 60.4 |
| 3.5 | 76.3 | 58.5 |
| 3.4 | 75.6 | 56.8 |
| 3.3 | 75.1 | 55.1 |
| 3.2 | 74.1 | 52.8 |

Example 5. Comparison of Mutated (Variant) mAbs Using Weighted Shoulder Score and Weighted Leader Score A set of 33 different antibodies, including a parental antibody sequence and 32 antibody variants each with a different variant amino acid sequence compared to a parental antibody sequence, were commercially generated with a range of 1 to 13 residues mutated relative to the parental sequence. The DSF thermograms for these antibodies were measured in phosphate buffered saline (PBS).

Figure 5:
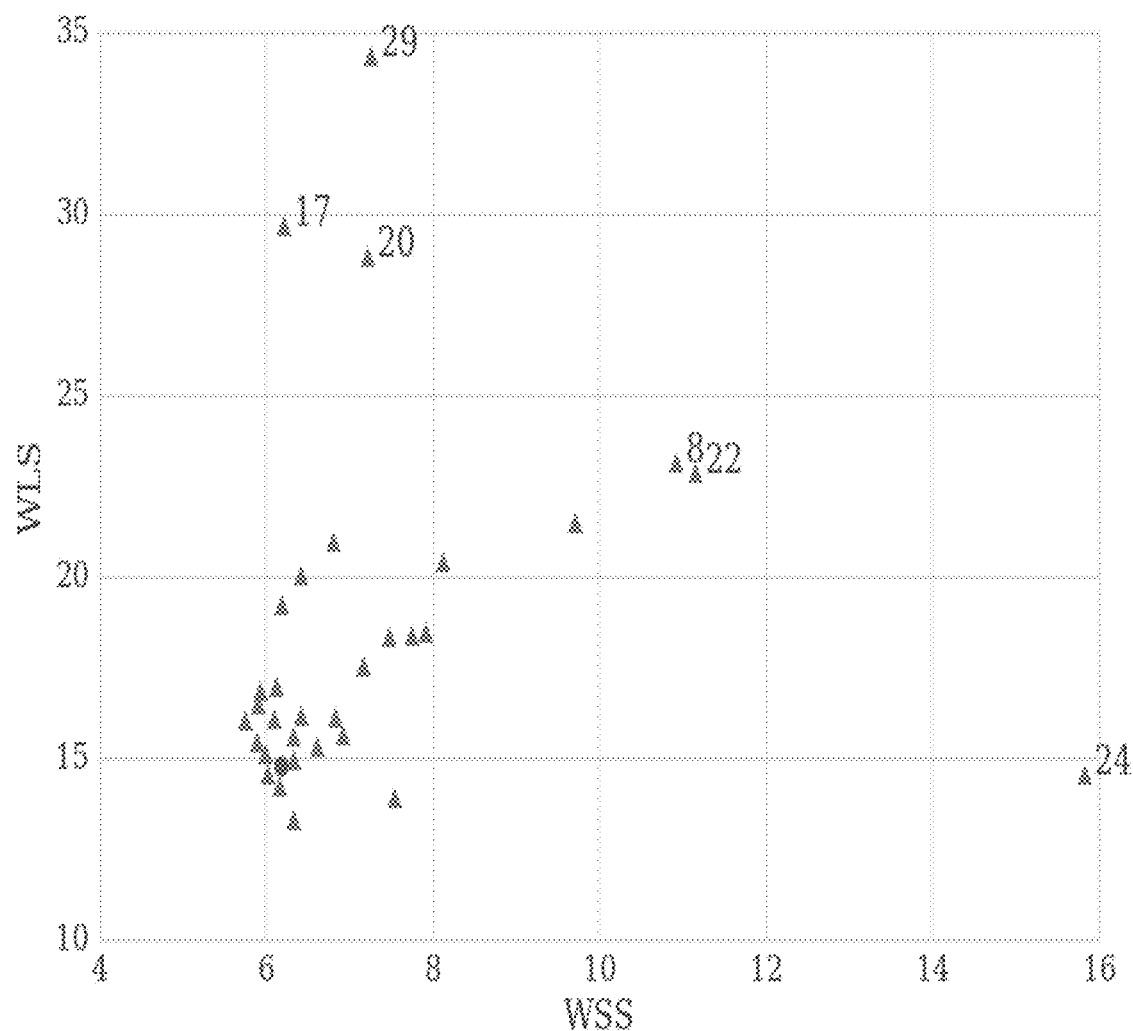
FIG. 5 illustrates the measured WSS and WLS values for 33 different antibody molecules tested, as plotted on x- and y-axes, respectively. The WSS and WLS values of the parental molecule are shown as a circle, while the WSS and WLS values of the variants are shown as triangles. The molecules with the most notable changes in WSS and WLS are indicated with their variant numbers and correspond to the thermograms shown in FIG. 6 herein.

The WSS value and WLS value were calculated in the manner described herein and are shown in Table 7, below, and illustrated in FIG. 5. The designated variant numbers shown in Table 7 and in FIG. 5 and FIG. 6 are unrelated to the Protein Numbers described in Table 1 hereinabove.

Many of the variant mutations had no effect on the thermogram (i.e., WSS and WLS were very similar to the parent), but others showed notable increase in high-temperature or low-temperature shoulder as indicated by the WSS and WLS scalar values, respectively.

Figure 6:
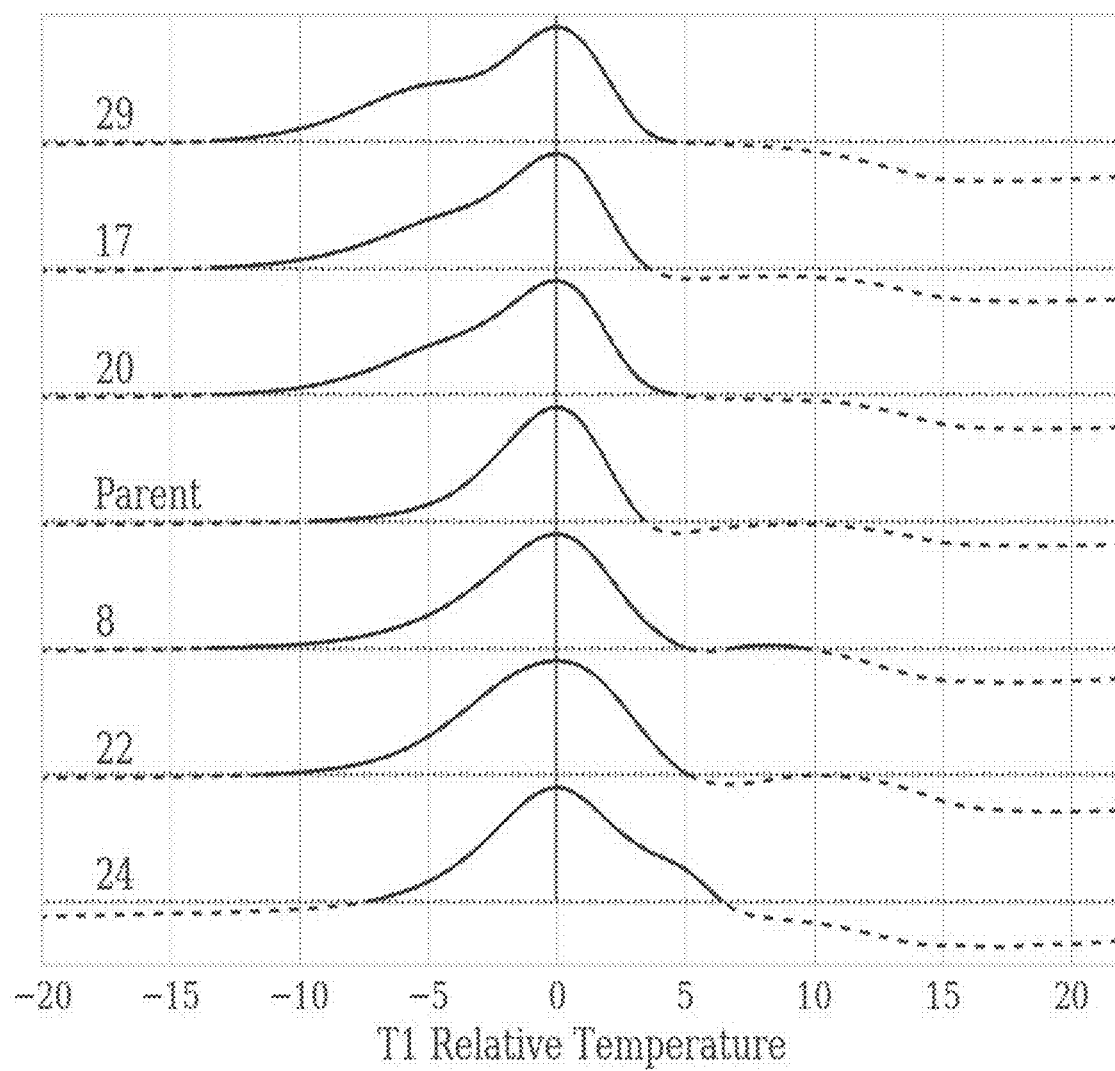
FIG. 6 shows thermograms for select samples of variants (sample number indicated on the left of each trace). Temperatures are relative to T1 such that each trace is centered at its T1. The three traces with the highest WSS (variants 8, 22, and 24, respectively) show increased high-temperature shoulder relative to the parent. The three traces with the highest WLS (variants 17, 20, and 29, respectively) showed increased low-temperature shoulder relative to the parental protein.

FIG. 6 shows the thermograms for several notable molecules (each centered to its T1). In these thermograms, the developing shoulders can be seen relative to the parent protein. An advantage of the WSS and WLS values here is that the small changes in the shoulder would be hard to identify through standard peak fitting but are clearly detected by the WSS and WLS.

From these results, individual mutations that are beneficial to the thermal stability of the protein can be identified for further investigation and development. To that end, the WSS and WLS values are also useful continuous-response metrics for developing machine-learning models that predict thermal stability.

TABLE 7

Weighted Shoulder Score (WSS) and Weighted Leader Score (WLS) values for all 32 antibody variants and the parent antibody molecule.

| Molecule (Variant # or Parent) | WSS | WLS |
|---|---|---|
| 1 | 7.2 | 17.6 |
| 2 | 7.5 | 18.4 |
| 3 | 6.4 | 20.1 |
| 4 | 8.1 | 20.4 |
| 5 | 6.4 | 16.2 |
| 6 | 6.8 | 21.0 |
| 7 | 6.2 | 19.2 |
| 8 | 10.9 | 23.1 |
| 9 | 5.9 | 16.9 |
| 10 | 6.3 | 15.6 |
| 11 | 6.6 | 15.3 |
| 12 | 6.8 | 16.2 |
| 13 | 6.9 | 15.7 |
| 14 | 6.2 | 14.3 |
| 15 | 6.0 | 15.2 |
| 16 | 6.3 | 13.3 |
| 17 | 6.2 | 29.7 |
| 18 | 6.3 | 15.0 |
| 19 | 6.1 | 17.0 |
| 20 | 7.2 | 28.9 |
| 21 | 6.1 | 16.1 |
| 22 | 11.2 | 22.9 |
| 23 | 7.5 | 13.9 |
| 24 | 15.8 | 14.6 |
| 25 | 6.0 | 14.6 |
| 26 | 5.8 | 16.1 |
| 27 | 5.9 | 16.5 |
| 28 | 7.8 | 18.4 |
| 29 | 7.3 | 34.4 |
| 30 | 7.9 | 18.5 |
| 31 | 9.7 | 21.5 |
| 32 | 5.9 | 15.4 |
| Parent Ab | 6.2 | 14.8 |

We claim:

1. A method for predicting the stability of a protein at low pH, comprising:
 (a) heating to a continuous set of temperatures in the range of about 20° C. to about 95° C. a first reaction mixture comprising a hydrophobic fluorescent dye and a protein of interest, at a first pH value in the range of about pH 4.0 to about pH 4.2, and:
  (i) detecting fluorescence of the dye over the range of temperatures to obtain a first fluorescence curve;
  (ii) obtaining the first derivative of the first fluorescence curve; and
  (iii) determining the temperature transitions of the protein of interest, at the first pH value, from the first derivative of the first fluorescence curve;
 (b) heating to a continuous set of temperatures in the range of about 20° C. to about 95° C. one or more second reaction mixture(s) comprising the hydrophobic fluorescent dye and the protein of interest, at one or more different second pH value(s) between about pH 2.9 to about pH 4.0, each different second pH value being lower than the first pH value, and:
  (i) detecting fluorescence of the dye in each of the one or more second reaction mixture(s) over the range of temperatures to obtain a second fluorescence curve for each second reaction mixture;
  (ii) obtaining the first derivative of each second fluorescence curve; and
  (iii) determining the temperature transitions of the protein of interest, at the one or more different second pH value(s), from the first derivative(s) of the second fluorescence curve(s); and
 (c) comparing the temperature transition peaks of the protein of interest at the first pH value and at the one or more different second pH value(s), wherein, if a temperature transition peak present at the first pH value is absent or shifted at one or more of the different second pH value(s), the protein of interest is predicted to display poor stability at low pH.

2. The method of claim 1, wherein determining the temperature transitions of the protein of interest from the first derivative of the first fluorescence curve or from the first derivative of each second fluorescence curve, or both, comprises:
 (a) locating on the first derivative of the first fluorescence curve a lowest temperature peak (the $T_1$ peak of the first fluorescence curve) having a maximum intensity of at least about 30% of the maximum intensity peak of the first derivative of the fluorescence curve, wherein the fluorescence intensity of the $T_1$ peak of the first fluorescence curve is $I_{T1}$, and the temperature at which the maximum $I_{T1}$ occurs is $T_{T1}$ of the first fluorescence curve; and
 (b) for each of the one or more second fluorescence curve(s), finding a peak closest in temperature to the:
  (i) $T_{T1}$ of the first fluorescence curve; or
  (ii) $T_{T1}$ of a different second fluorescence curve obtained from a different second reaction mixture with a different pH value closest to its pH value;
 and designating that peak the $T_1$ peak of the second fluorescence curve, wherein the fluorescence intensity of the $T_1$ peak of each second fluorescence curve is the $I_{T1}$ of the second fluorescence curve and the temperature at which the maximum $I_{T1}$ of the second fluorescence curve occurs is the $T_{T1}$ of the second fluorescence curve;
 (c) calculating the fluorescence intensity value (I) of all points of the first derivative of each of the first fluorescence curve and the one or more second fluorescence curve(s) normalized to its $I_{T1}$ ($I_{norm}$), wherein $I_{norm} = I/I_{T1}$;
 (d) calculating a relative temperature value ($T_{rel}$) of all points of the first derivative of each fluorescence curve relative to its $T_{T1}$, wherein, $T_{rel} = T - T_{T1}$;
 (e) calculating a weight ($W_{WSS}$) of all points of the first derivative of the fluorescence curve, wherein:

$$W_{WSS} = \begin{cases} T_{rel}^2, & \text{if } (T_{rel} > 0 \text{ and } I_{norm} > 0) \\ 0, & \text{otherwise} \end{cases};$$

and
 (f) subsequently calculating a scalar weighted shoulder score (WSS), wherein:

$$\text{WSS} = \sqrt{I_{norm} W_{WSS}},$$

wherein the position and shape of a second temperature transition ($T_2$) peak and/or a third temperature transition ($T_3$) peak characteristic of the unfolding of the protein of interest are detected as increases in the scalar WSS value.

3. The method of claim 2, further comprising:
 (g) calculating a weight ($W_{WLS}$) of all points of the first derivative of the first fluorescence curve and of the first derivative of each second fluorescence curve, wherein for all transitions prior to the $T_1$ peak of the first fluorescence curve or prior to the $T_1$ peak of each second fluorescence curve, respectively, $T_{rel}=T_{T1}-T$, and wherein:

$$W_{WLS} = \begin{cases} T_{rel}^2, & \text{if } (T_{rel} > 0 \text{ and } I_{norm} > 0) \\ 0, & \text{otherwise} \end{cases};$$

and (h) subsequently calculating a scalar weighted leader score (WLS), wherein:

$$WLS = \sqrt{I_{norm}W_{WLS}},$$

wherein the position and shape of any lower temperature transition peak at a $T_{0, -1, -2, etc.}$, less than $T_1$ characteristic of the unfolding of the protein of interest are detected as increases in the scalar WLS value.

4. The method of claim 1, wherein the protein of interest is an immunoglobulin.

5. The method of claim 1, wherein the protein of interest is a fusion protein.

6. The method of claim 1, wherein the method is employed to predict the suitability of the protein of interest for low pH viral inactivation.

7. The method of claim 1, wherein the method is employed to interrogate the conformational stability of the protein of interest.

8. The method of claim 7, wherein the method is employed to detect Fc glycosylation heterogeneity.

9. A method for interrogating the physiochemical properties of a protein of interest, comprising:
   (a) heating to a continuous set of temperatures, each temperature being a value of T in the range of about 20° C. to about 95° C., a reaction mixture comprising a hydrophobic fluorescent dye and a protein of interest in a buffer, which contains a physiochemical stressor of interest at a reference concentration greater than or equal to zero, and:
      (i) detecting fluorescence of the dye over the range of temperatures to obtain a first fluorescence curve; and
      (ii) obtaining the first derivative of the first fluorescence curve;
   (b) heating to a continuous set of temperatures in the range of about 20° C. to about 95° C. one or more second reaction mixture(s) comprising the hydrophobic fluorescent dye and the protein of interest, at one or more different second concentration value(s) of the physiochemical stressor of interest, each different second concentration value being greater than the reference concentration, and:
      (i) detecting fluorescence of the dye in each of the one or more second reaction mixture(s) over the range of temperatures to obtain a second fluorescence curve for each second reaction mixture; and
      (ii) obtaining the first derivative of each second fluorescence curve;
   (c) determining the temperature transitions of the protein of interest from the first derivative of the first fluorescence curve or from the first derivative of each second fluorescence curve, or both, which comprises:
      (i) locating on the first derivative of the first fluorescence curve a lowest temperature peak (the $T_1$ peak of the first fluorescence curve) having a maximum intensity of at least about 30% of the maximum intensity peak of the first derivative of the fluorescence curve, wherein the fluorescence intensity of the $T_1$ peak of the first fluorescence curve is $I_{T1}$, and the temperature at which the maximum $I_{T1}$ occurs is $T_{T1}$ of the first fluorescence curve; and
      (ii) for each of the one or more second fluorescence curve(s), finding a peak closest in temperature to the:
         (1) $T_{T1}$ of the first fluorescence curve; or
         (2) $T_{T1}$ of a different second fluorescence curve obtained from a different second reaction mixture with a different second concentration value closest to its second concentration value; and designating that peak the $T_1$ peak of the second fluorescence curve, wherein the fluorescence intensity of the $T_1$ peak of each second fluorescence curve is the $I_{T1}$ of the second fluorescence curve and the temperature at which the maximum $I_{T1}$ of the second fluorescence curve occurs is the $T_{T1}$ of the second fluorescence curve;
      (iii) calculating the fluorescence intensity value (I) of all points of the first derivative of each of the first fluorescence curve and the one or more second fluorescence curve(s) normalized to its $I_{T1}$ ($I_{norm}$), wherein $I_{norm}=I/I_{T1}$;
      (iv) calculating a relative temperature value ($T_{rel}$) of all points of the first derivative of each fluorescence curve relative to its $T_{T1}$, wherein, $T_{rel}=T-T_{T1}$;
      (v) calculating a weight ($W_{WSS}$) of all points of the first derivative of the fluorescence curve, wherein:

$$W_{WSS} = \begin{cases} T_{rel}^2, & \text{if } (T_{rel} > 0 \text{ and } I_{norm} > 0) \\ 0, & \text{otherwise} \end{cases};$$

and
      (vi) subsequently calculating a scalar weighted shoulder score (WSS), wherein:

$$WSS = \sqrt{I_{norm}W_{WSS}},$$

wherein the position and shape of a second temperature transition ($T_2$) peak and/or a third temperature transition ($T_3$) peak characteristic of the unfolding of the protein of interest are detected as increases in the scalar WSS value; and (d) comparing the temperature transition peaks of the protein of interest at the reference concentration and at the one or more different second concentration value(s) of the physiochemical stressor of interest, wherein, if a temperature transition peak present at the reference concentration is absent or shifted at one or more of the different second concentration value(s) of the physiochemical stressor of interest, the protein of interest is shown to display poor stability in response to the physiochemical stressor of interest.

10. The method of claim 9, further comprising:
   (e) calculating a weight ($W_{WLS}$) of all points of the first derivative of the first fluorescence curve and of the first derivative of each second fluorescence curve, wherein for all transitions prior to the $T_1$ peak of the first fluorescence curve or prior to the $T_1$ peak of each second fluorescence curve, respectively, $T_{rel}=T_{T1}-T$, and:

$$W_{WLS} = \begin{cases} T_{rel}^2, & \text{if } (T_{rel} > 0 \text{ and } I_{norm} > 0) \\ 0, & \text{otherwise} \end{cases};$$

and
(f) subsequently calculating a scalar weighted leader score (WLS), wherein:

$$WLS = \sqrt{I_{norm} W_{WLS}},$$

wherein the position and shape of any lower temperature transition peak at a $T_{0, -1, -2, etc.}$, less than $T_1$ characteristic of the unfolding of the protein of interest are detected as increases in the scalar WLS value.

11. The method of claim 9, wherein the protein of interest is an immunoglobulin.

12. The method of claim 9, wherein the protein of interest is a fusion protein.

13. The method of claim 9, wherein the physiochemical property of the protein of interest is stability at low pH.

14. The method of claim 9, wherein the physiochemical property of the protein of interest is conformational stability.

15. The method of claim 14, wherein the method is employed to detect Fc glycosylation heterogeneity.

16. The method of claim 14, wherein the physiochemical property of the protein of interest is thermal stability.

17. The method of claim 9, wherein the physiochemical property of the protein of interest is ANS dye binding to evaluate extrinsic fluorescence binding.

18. The method of claim 9, wherein the physiochemical property of the protein of interest is measurement and interpretation curves of intrinsic fluorescence.

* * * * *